(12) United States Patent
Baetscher et al.

(10) Patent No.: US 6,703,209 B1
(45) Date of Patent: Mar. 9, 2004

(54) PORCINE TOTIPOTENT CELLS AND METHOD FOR LONG-TERM CULTURE

(75) Inventors: Manfred Baetscher, Portland, OR (US); Gottfried Brem, Hilgetshausen-Tandem (DE)

(73) Assignee: Biotransplant, Inc., Charlestown, MA (US)

( * ) Notice: Subject to any disclaimer, the term of this patent is extended or adjusted under 35 U.S.C. 154(b) by 0 days.

(21) Appl. No.: 09/133,352

(22) Filed: Aug. 13, 1998

(51) Int. Cl.$^7$ .................. G01N 33/567; C12N 15/00; C12N 5/02; C12N 15/63
(52) U.S. Cl. .................. 435/7.21; 435/320.1; 435/325; 435/455
(58) Field of Search .............. 435/325, 320.1, 435/455, 7.21; 800/17, 21, 22, 25

(56) References Cited

U.S. PATENT DOCUMENTS

| | | | |
|---|---|---|---|
| 5,453,357 A | 9/1995 | Hogan | 435/7.21 |
| 5,589,582 A | * 12/1996 | Hawley et al. | 536/23.5 |
| 5,690,926 A | 11/1997 | Hogan | 424/93.1 |
| 5,994,619 A | * 11/1999 | Stice et al. | 800/21 |

FOREIGN PATENT DOCUMENTS

| | | |
|---|---|---|
| WO | WO94/09803 | 5/1994 |
| WO | WO95/34636 | 12/1995 |
| WO | 95/34636 | * 12/1995 |
| WO | WO96/14410 | 5/1996 |
| WO | WO97/20035 | 6/1997 |
| WO | WO98/16630 | 4/1998 |

OTHER PUBLICATIONS

Moreadith et al., Journal of Molecular Medicine, vol. 75, pp. 208–216, 1997.*
Wheeler, Reproduction, Fertility and Development, vol. 6, pp. 563–568, 1994.*
Notarianni et al., Journal of Reproduction and Fertility, vol. 41, pp. 51–56, 1990.*
Matsui, et al., "Cell", vol. 70, pp. 841–847 (Sep. 4, 1992).
Resnick, et al., "Nature", vol. 359, pp. 550–551 (Oct. 8, 1992).
Liu, et al., "Int. J. Dev. Biol.", vol. 39, pp. 639–644 (1995).
Piedrahita, et al., "J. Repro. and Fert. Supp.", vol. 52, pp. 245–254 (1997).
Takagi, et al., "Mol. Repro. and Dev.", vol. 46, pp. 567–580 (1997).
Shim, et al., "Biology of Reproduction", vol. 57, pp. 1089–1095 (1997).
Piedrahita, et al., "Biology of Reproduction", vol. 58, pp. 1321–1329 (1998).
Zhang, et al., "Biology of Reproduction", vol. 50, pp. 95–102 (1994).

* cited by examiner

*Primary Examiner*—Deborah Crouch
*Assistant Examiner*—Joseph Woitach
(74) *Attorney, Agent, or Firm*—Elliot M. Olstein; Raymond J. Lillie

(57) ABSTRACT

This invention provides a method of using a porcine stem cell factor (PSCF), which may also be termed porcine "steel" factor, which is preferably membrane-bound PSCF on transfected murine STO feeder cells, for establishing pluripotent or totipotent porcine cell lines, especially for the culture of porcine primordial germ cells (PGCs).

12 Claims, 20 Drawing Sheets

FIG. 3A

```
TCCAGA ACAGGTAAAC GGAGTTGCCA CACCGCTGCC TGGGCTGGAT CACAGCGCTG                    60

TCCTT ATG AAG AAG ACA CAA ACT TGG ATT ATC ACT TGC ATT TAT                      108
      Met Lys Lys Thr Gln Thr Trp Ile Ile Thr Cys Ile Tyr
      -25                                            -15

CAA CTG CTC CTA TTT AAT CCT CTC GTC AGA ACT CAA GGG ATC TGC                    156
Gln Leu Leu Leu Phe Asn Pro Leu Val Arg Thr Gln Gly Ile Cys
              -10                      -5                1

AAC CGT GTG ACT GAT GAT GTG AAA GAC GTT ACA AAA TTG GTG GCA                    204
Asn Arg Val Thr Asp Asp Val Lys Asp Val Thr Lys Leu Val Ala
                                          15                 20

CTT CCA AAA GAC TAT AAG ATA ACC CTC AAA TAT GTC CCC GGG ATG                    252
Leu Pro Lys Asp Tyr Lys Ile Thr Leu Lys Tyr Val Pro Gly Met
                25                        30                 35

GTT TTG CCT AGT CAT TGT TGG ATA AGC GAA ATG GTG GAA CAA CTG                    300
Val Leu Pro Ser His Cys Trp Ile Ser Glu Met Val Glu Gln Leu
              40                         45                 50

GTC AGC TTG ACT GAT CTT CTG GAC AAG TTT TCC AAT ATT TCT GAA                    348
Val Ser Leu Thr Asp Leu Leu Asp Lys Phe Ser Asn Ile Ser Glu
              55                         60                 65

TTG AGT AAT TAT TCT ATA GAC AAA CTT GTG AAA ATT GTT GAT                        396
Leu Ser Asn Tyr Ser Ile Ile Asp Lys Leu Val Lys Ile Val Asp
70                         75                 80

CTC GTG GAA TGC ATG GAA GAA CAC TCA TTT ACT GAG AAT GTA AGA AAA                444
Leu Val Glu Cys Met Glu Glu His Ser Phe Thr Glu Asn Val Arg Lys
              85                         90                      100

TCT AAG AGC CCA GAA CCC AGG CTG TTT ACT CCT GAA AAA TTC TTT                    492
Ser Lys Ser Pro Glu Pro Arg Leu Phe Thr Pro Glu Lys Phe Phe
      105                       110                     115

ATT TTT AAT AGA TCC ATC GAT GCC TTC AAG GAT TTG GAG ATG GTG                    540
Ile Phe Asn Arg Ser Ile Asp Ala Phe Lys Asp Leu Glu Met Val
```

MATCH FIG. 3A WITH FIG. 3B

MATCH FIG. 3B WITH FIG. 3A

FIG. 3B

```
                        120                 125                 130
CCT AAA ACT AGT GAA TGT GTG ATT TCT TCA ACA TTA ACT CCT GAA       588
Pro Lys Thr Ser Glu Cys Val Ile Ser Ser Thr Leu Thr Pro Glu
    135                 140                 145

GAT TCC AGA GTC AGT GTC ACA AAA CCA TTT ATG TTA CCC CCT GTT       636
Asp Ser Arg Val Ser Val Thr Lys Pro Phe Met Leu Pro Pro Val
150                 155                 160

GCC AGC TCC CTT AGG AAT GAC AGC AGT AGC AGT AAT AGG AAA GCC       684
Ala Ser Ser Leu Arg Asn Asp Ser Ser Ser Ser Asn Arg Lys Ala
            170                 175                 180

GAT TCG ATT GAA GAC TCC AGC CTC CAG TGG GCA GCG GTA GCA TTG       732
Asp Ser Ile Glu Asp Ser Ser Leu Gln Trp Ala Ala Val Ala Leu
        185                 190                 195

GCA TTC TTC TCT CTT GTG ATT GGG TTT GCT TTT GGA GCC TTA TAC       780
Ala Phe Phe Ser Leu Val Ile Gly Phe Ala Phe Gly Ala Leu Tyr
    200                 205                 210

AAG AAG AAA CAA CCA AAC CTT ACA AGG ACA GTG GAA AATAATA GAG       828
Lys Lys Lys Gln Pro Asn Leu Thr Arg Thr Val Glu Asn Ile Gln
215                 220                 225

AAT GAA GAG GAT AAT AGT ATA AGT ATG TTG CAA GAA AAA GAG AGA       876
Asn Glu Glu Asp Asn Ser Ile Ser Met Leu Gln Glu Lys Glu Arg
230                 235                 240

TTT CAA GAA GTG TAA TTGTGGCGTG TATCAACACT GTTGCTTTCG TACATTGGGT   934
Phe Gln Glu Val

ACAGTT GATGTTTG                                                   952
```

FIG. 4A

```
                                                    GCGCT GCCTTCCTT                           15

ATG AAG AAG ACA CAA ACT TGG ATT ATC ACT TGC ATT TAT CTT CAA CTG             63
Met Lys Lys Thr Gln Thr Trp Ile Ile Thr Cys Ile Tyr Leu Gln Leu
-25                      -20                      -15                -10

CTC CTA TTT AAT CCT CTC GTC AGA ACT CAA GGG ATC TGC AGG AAC CGT            111
Leu Leu Phe Asn Pro Leu Val Arg Thr Gln Gly Ile Cys Arg Asn Arg
         -5                       1                        5

GTG ACT GAT GAT AAA GAC GTT ACA AAA TTG GTG GCA AAT CTT CCA                159
Val Thr Asp Asp Lys Asp Val Thr Lys Leu Val Ala Asn Leu Pro
              10                      15                       20

AAA GAC TAT AAG ATA ACC CTC AAA TAT GTC CCC GGG ATG GAC GTT TTG            207
Lys Asp Tyr Lys Ile Thr Leu Lys Tyr Val Pro Gly Met Asp Val Leu
         25                      30                       35

CCT AGT CAT TGT TGG ATA AGC GAA ATG GTG GAA CAA CTG TCA GTC AGC            255
Pro Ser His Cys Trp Ile Ser Glu Met Val Glu Gln Leu Ser Val Ser
40                       45                       50              55

TTG ACT GAT CTT CTG GAC AAG TTT TCC AAT ATT TCT GAA GGC TTG AGT            303
Leu Thr Asp Leu Leu Asp Lys Phe Ser Asn Ile Ser Glu Gly Leu Ser
```

MATCH FIG. 4A WITH FIG. 4B

FIG. 4B

MATCH FIG. 4B WITH FIG.4A

```
AAT TAT TCT ATC ATA GAC AAA CTT GTG AAA ATT GTT GAT GAC CTC GTG         351
Asn Tyr Ser Ile Ile Asp Lys Leu Val Lys Ile Val Asp Asp Leu Val
            75                      80                      85

GAA TGC ATG GAA GAA CAC TCA TTT GAG AAT GTA AGA AAA TCA TCT AAG         399
Glu Cys Met Glu Glu His Ser Phe Glu Asn Val Arg Lys Ser Ser Lys
            90                      95                     100

AGC CCA GAA CCC AGG CTG TTT ACT CCT GAA AAA TTC TTT GGG ATT TTT         447
Ser Pro Glu Pro Arg Leu Phe Thr Pro Glu Lys Phe Phe Gly Ile Phe
           105                     110                     115

AAT AGA TCC ATC GAT GCC TTC AAG GAT TTG GAG ATG GTG GCA CCT AAA         495
Asn Arg Ser Ile Asp Ala Phe Lys Asp Leu Glu Met Val Ala Pro Lys
           120                     125                     135

ACT AGT GAA TGT GTG ATT TCT TCA ACA TTA ACT CCT GAA AAA GAT TCC         543
Thr Ser Glu Cys Val Ile Ser Ser Thr Leu Thr Pro Glu Lys Asp Ser
           140                     145                     150

AGA GTC AGT GTC ACA AAA CCA TTT ATG TTA CCC CCT GTT GCA GCC AGC         591
Arg Val Ser Val Thr Lys Pro Phe Met Leu Pro Pro Val Ala Ala Ser
           155                     160                     165

TCC CTT AGG AAT GAC AGC AGT AGC AGT AAT AGG AAA GCC TAA                 633
Ser Leu Arg Asn Asp Ser Ser Ser Ser Asn Arg Lys Ala
           170                     175                     180
```

FIG. 6A

```
CGCTGCCTTT CCTT ATG AAG ACA CAA ACT TGG ATT ATC ACT TGC ATT                    50
              Met Lys Lys Thr Gln Thr Trp Ile Ile Thr Cys Ile
              -25                 -20                 -15

TAT CTT CAA CTG CTC CTA TTT AAT CCT CTC GTC AGA ACT CAA GGG ATC                98
Tyr Leu Gln Leu Leu Leu Phe Asn Pro Leu Val Arg Thr Gln Gly Ile
            -10                  -5                   1

TGC AGG AAC CGT GTG ACT GAT GAT GTG AAA GAC GTT ACA AAA TTG GTG               146
Cys Arg Asn Arg Val Thr Asp Asp Val Lys Asp Val Thr Lys Leu Val
  5                   10                  15

GCA AAT CTT CCA AAA GAC TAT AAG ATA ACC CTC AAA TAT GTC CCC GGG               194
Ala Asn Leu Pro Lys Asp Tyr Lys Ile Thr Leu Lys Tyr Val Pro Gly
        20                  25                  30                  35

ATG GAC GTT CCT AGT CAT TGT TGG ATA AGC GAA ATG GTG GAA CAA                   242
Met Asp Val Leu Pro Ser His Cys Trp Ile Ser Glu Met Val Glu Gln
            40                  45                  50

CTG TCA GTC AGC TTG ACT GAT CTT CTG GAC AAG TTT TCC AAT ATT TCT               290
Leu Ser Val Ser Leu Thr Asp Leu Leu Asp Lys Phe Ser Asn Ile Ser
            55                  60                  65

GAA GGC TTG AGT AAT TAT TCT ATC ATA GAC AAA CTT GTG AAA ATT GTT               338
Glu Gly Leu Ser Asn Tyr Ser Ile Ile Asp Lys Leu Val Lys Ile Val
            70                  75                  80

GAT GAC CTC GTG GAA TGC ATG GAA GAA CAC TCA TTT GAG AAT GTA AGA               386
Asp Asp Leu Val Glu Cys Met Glu Glu His Ser Phe Glu Asn Val Arg
        85                  90                  95

AAA TCA AAG AGC CCA GAA CCC AGG CTG TTT ACT CCT GAA AAA TTC                   434
Lys Ser Lys Ser Pro Glu Pro Arg Leu Phe Thr Pro Glu Lys Phe
            100                 105                 110                 115

TTT GGG ATT TTT AAT AGA TCC ATC GAT GCC TTC AAG GAT TTG GAG ATG               482
Phe Gly Ile Phe Asn Arg Ser Ile Asp Ala Phe Lys Asp Leu Glu Met
```

MATCH FIG.6A WITH FIG.6B

FIG. 6B

MATCH FIG. 6B WITH FIG. 6A

```
                    120                     125                    130
GTG GCA CCT AAA ACT AGT GAA TGT GTG ATT TCT TCA ACA TTA ACT CCT           530
Val Ala Pro Lys Thr Ser Glu Cys Val Ile Ser Ser Thr Leu Thr Pro
                135                     140                    145

GAA AAA GGG AAT GAC AGC AGT AGC AGT AAT AGG AAA GCC TCA GAT TCG           578
Glu Lys Gly Asn Asp Ser Ser Ser Ser Asn Arg Lys Ala Ser Asp Ser
            150                     155                    160

ATT GAA GAC TCC AGC CTC CAG TGG GCA GCG GTA GCA TTG CCA GCA TTC           626
Ile Glu Asp Ser Ser Leu Gln Trp Ala Ala Val Ala Leu Pro Ala Phe
        165                     170                    175

TTC TCT CTT GTG ATT GGG TTT GCT TTT GGA GCC TTA TAC TGG AAG AAG           674
Phe Ser Leu Val Ile Gly Phe Ala Phe Gly Ala Leu Tyr Trp Lys Lys
    180                     185                    190                195

AAA CAA CCA AAC CTT ACA AGG ACA GTG GAA AAT ATA GAG ATT AAT GAA           722
Lys Gln Pro Asn Leu Thr Arg Thr Val Glu Asn Ile Glu Ile Asn Glu
                200                     205                    210

GAG GAT AAT GAG ATA AGT ATG TTG CAA GAA AAA GAG CAG GAG TTT CAA           770
Glu Asp Asn Glu Ile Ser Met Leu Gln Glu Lys Gln Glu Arg Glu Phe Gln
            215                     220                    225

GAA GTG TAA TTGTGGGGTG TATCAACACT GTTGCTTTCG TACATTGGGT GGTTCTAGA        828
Glu Val
```

PORCINE TOTIPOTENT CELLS AND METHOD FOR LONG-TERM CULTURE

This invention relates to totipotent porcine cells and to the recovery, proliferation and use thereof. The invention further relates to the use of a porcine stem cell factor (pSCF), which may also be termed porcine "steel" factor, which is preferably membrane-bound pSCF on transfected murine STO feeder cells, for establishing pluripotent or totipotent porcine cell lines, especially for the culture of porcine primordial germ cells (PGCs).

PGCs are precursor cells of the germ line in the developing embryo. In swine (porcine) embryos PGCs migrate from the base of the allantois through the hindgut epithelium and dorsal mesentery to colonize the gonadal anlage. During the migration to the genital ridge the PGCs increase in number in pigs to approximately $1 \times 10^6$ by day 50. Porcine PGCs can be distinguished from somatic cells by their morphology: large nuclei, high nuclei-cytoplasm-ratio, occasional blebbing and by clearly visible pseudopodia.

Totipotent cell lines have been obtained from primordial germ cells (PGCs) in mice. Such pluripotent or totipotent cell lines are important in the field of transgenic animals. Several methods for producing transgenic animals, including a microinjection method, exist and are well-known in the art. However, a drawback to the microinjection method is that providing transgenic animals into whom genes can be embedded at will in their chromosomes is difficult.

Fortunately, producing such transgenic animals is made potentially possible by using totipotent or pluripotent cells such as embryonic stem (ES) cells to establish a transgenic animal line. For example, ES cells can be injected into a mouse embryo near the embryonic location which will give rise to germ cells in the resulting adult mouse, and result in functional germ cells originating from the injected ES cells. Therefore, such adult mouse can produce offspring that have the traits of the injected ES cells. If the ES cells have been altered genetically prior to their injection into the embryo such offspring of the resulting adult mice can form a chimeric line of mice with the genetically altered trait.

Accordingly, an ES cell line maintained in culture in a mouse can be utilized for a variety of gene introduction methods (for example, the retrovirus vector method, the electroporation method and the calcium phosphate method) and then injected into embryos as part of a process to produce chimeras with desired altered genetic traits. With such a procedure it is possible to obtain an individual which has been altered at a specific gene locus by substitution of a desired gene, whether active or inactive, for the original gene by homologous recombination following insertion of the gene into the ES cell.

Through the totipotent-cell-embryo-injection-method precise alteration of a single gene trait and the study of a specific gene function in a resulting chimeric animal line is possible.

Also, in such chimeric lines it would be possible through such precise genetic manipulation to cause tissue protein changes and remove certain native antigens so that an organ or tissue from the chimeric animal could be transferred to another species without rejection by the other species.

In mice, primordial germ cells isolated during their migratory phase and cultured on feeders layers (e.g., fetal fibroblast cells ("STO cells"), Kawase et al. *Experimental Medicine*, Vol. 10, No. 13, 1575 to 1580 (1992)) with leukaemia inhibitory factor (LIF) and mouse stem cell factor (MSCF) provide mice PGCs that result in cell lines for long-term culture. In addition, mice PGCs can also be cultured in similar media to which basic fibroblast growth factor (bFGF) has been added, thereby converting PGCs to cells that resemble undifferentiated embryonic stem cells (ESs) (Matsui et al., Cell 1992 70:5:841–847; Resnick et al., Nature 1992 359 (6395):550–551). Such (embryonic germ cell derived lines ("EGs") derived from PGCs can be utilized to contribute to the germ-line of chimeric mice. Early culture mice PGCs, cultured in the presence of LIF and MSCF, can be observed as burst colonies of cells with a flattened and polarized morphology that are characteristic of motile cells. By contrast, mice ESs or EGs derived from PGCs (e.g., long-term cultures) tend to form discrete colonies of tightly packed cells and resemble in morphology the germ cells observed in vivo when PGCs migrate to the germ layers in the embryo, differentiate into germ cells and establish colonies in the germ layer.

Quiescent descendants of ESs or EGs (long term cultures or germ cells from differentiated PGCs), which are observed to form tightly packed colonies rather than burst colonies, often require less growth factors or simple nutrients to continue proliferating. These totipotent germ cell lines, thus established, can be maintained in culture (by recycling to fresh media) and used to inject embryos, or alternatively can be frozen, thawed and then used.

Authors of work with mice PGCs, ESs or EGs have hypothesized that results with mice embryos could lead to similar results with other species. They hypothesized that it might be possible to use PGCs from other species along with such mice feeder cells which produce MSCF and LIF (such as transfected murine STO cells) for the establishment of totipotent cell-lines in domestic animals.

The classical ways of establishing pluripotent embryonic stem cells involve culturing of a preimplanted embryo or an enucleated egg which has been implanted with an isolated inner cell mass (ICM). Although this is routinely performed in mice, unfortunately, modified protocols in attempts to establish similar lines in domestic animals such as pigs have not been very successful. Such is evidenced by the inability of such lines to colonize somatic tissues or to provide a germ line of chimeric animals. This may be due to the fact that, unlike the mouse, ungulates have slowly proliferating early embryos with very low cell numbers. Therefore, until now, obtaining cell lines from domestic animals such as pigs has not been done successfully. Whether such procedures would even work with PGCs from domestic animals has remained an open and debatable question in the scientific community.

Accordingly, there is a need for establishment of totipotent/pluripotent cell lines from domestic animals, for example swine. Relative to other domestic animals, swine (or pigs) are easy to feed and maintain. Also, they have no reproductive season, can produce a fairly large number of fetuses, and provide offspring after only a relatively short gestation period.

Establishment of porcine pluripotent or totipotent PGC lines as an alternative to embryonic stem cells (ESCs) would be useful for studies of cell differentiation and gene regulation during embryonic development. Such lines would be important for the generation of transgenic pigs especially for their use in gene farming or xenotransplantation.

BRIEF DESCRIPTION OF THE FIGURES

FIG. 3 illustrates the full-length sequence for pSCF (SEQ ID NO:2) based on native cDNA (SEQ ID NO:1) as reported in Biology of Reproduction 50: 95–102 (1994).

FIG. 4 illustrates the polynucleotide sequence (SEQ ID NO:5) of a soluble form of pSCF from U.S. Pat. No. 5,589,582.

FIG. 6 illustrates the polynucleotide sequence (SEQ ID NO:8) of an active membrane-bound form of pSCF from which exon 6 has been been removed and replaced with a tri-nucleotide that encodes the amino acid "Gly" (SEQ ID NO:9), which is part of plasmid PPSCF.

In FIG. 7A PGCs are identified by alkaline phosphatase activity 1 day after isolation from embryos and plating onto STO8 feeder cells in ESC medium supplemented with LIF. PGCs exist as single cells. FIG. 7B shows three days after isolation that PGCs form small colonies. FIG. 7C shows five days after isolation that PGCs are found in larger colonies. Each of FIGS. 7A–7C are photographs formed at a magnification of 50×.

FIG. 9A shows that some colonies have become multilayered. FIG. 9B shows that some colonies grow as a monolayer on STO8 cells and contain only a small number of strongly stained cells together with AP negative cells.

SUMMARY OF THE INVENTION

Figure 1:
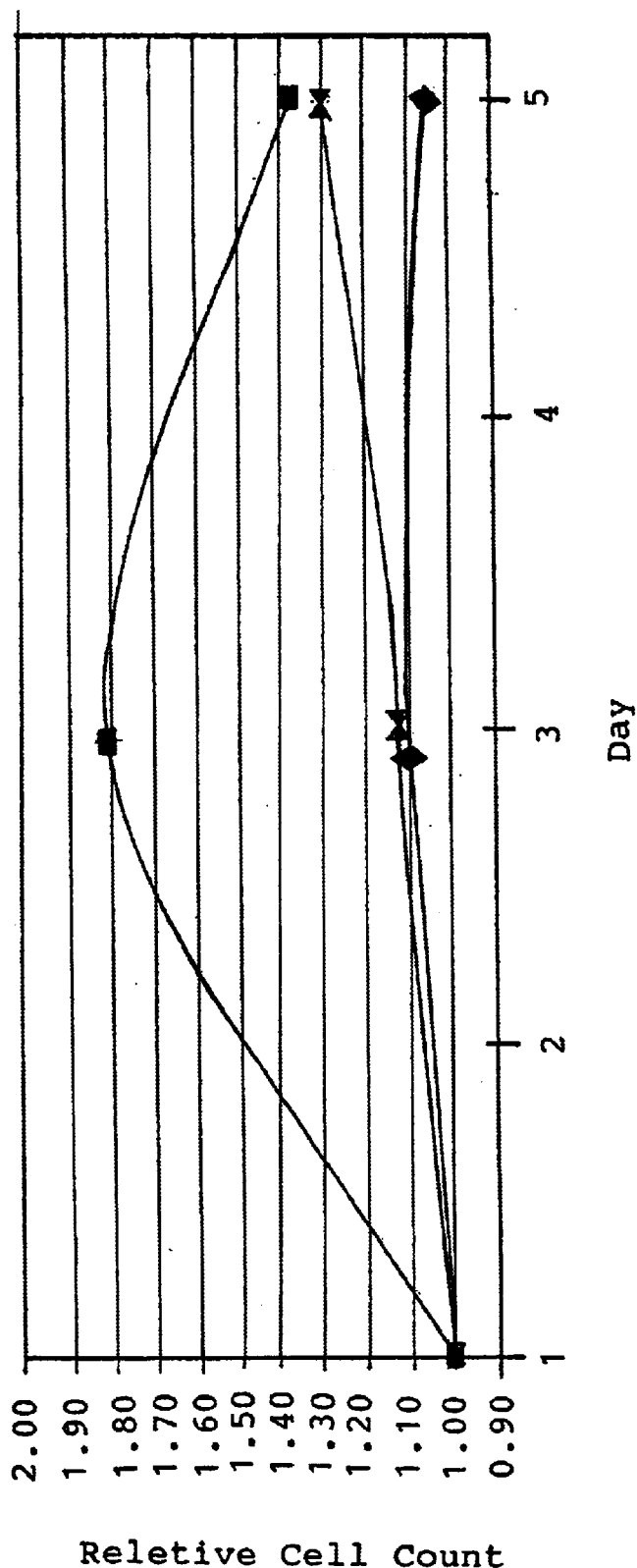
FIG. 1 illustrates the number of PGCs (relative to the number of PGCs present on the first day) in non-passaged initial cultures on days 1, 3 and 5 days when cultured on STO feeder cells (producing MSCF) in three out of four different culture media. The three plot lines represent three out of the four different culture conditions used: (1) ES medium (control) that is supplemented with 15% FCS (ES), (2) ES medium supplemented with growth factors LIF (ES+LIF), (3) ES medium supplemented with LIF plus bFGF (ES+LIF+bFGF) and (3) conditioned medium prepared from carcinoma cell line 5637.

In accordance with one aspect of the present invention, there is provided porcine totipotent cells.

In accordance with a further aspect of the present invention there is provided porcine primordial germ cells.

In accordance with yet another aspect, the invention provides porcine embryonic germ cells.

In yet a further aspect, there is provided porcine embryonic stem cells.

More particularly, the porcine totipotent cells of the invention may be recovered from the genital ridge and then cultured in the presence of porcine stem cell factor to thereby maintain, preserve and proliferate totipotent porcine cells. The porcine stem cell factor may be a soluble form (as described in U.S. Pat. No. 5,589,582) or may be a membrane-bound form of porcine stem cell factor as hereinafter described. The totipotent porcine cells are preferably maintained and caused to proliferate in the form of PGCs or EGs.

In accordance with an aspect of the present invention there is provided a totipotent porcine cell line obtained from culturing porcine PGCs that can be successfully cultured long-term and can survive cryopreservation while retaining totipotency. Preferably, such totipotent cell line is a germ cell line or a long-term culture PGC cell line. In a further preferred aspect such totipotent cell line is obtained from genetically altered embryonic cells having a trait that can be assayed for to ascertain when a chimeric animal is derived from such totipotent cells.

A further object is to provide a method for recovering and/or maintaining totipotent porcine cells (whatever the source, e.g., from PGCs, stem cells, germ cells or manufactured totipotent cells) and causing such totipotent cells to proliferate. In a preferred aspect such method provide for long-term culturing of such totipotent cells without a loss of totipotency.

Another object of the present invention is to provide a method for culturing PGCs, or totipotent cell lines obtained from PGCs, in the presence of porcine stem cell factor, which is preferably membrane-bound PSCF, to obtain or maintain a totipotent cell line from such PGCs. In a preferred aspect such method provides a process for maintaining a line of porcine PGCs in an undifferentiated state by culturing such PGCs for a culture cycle, obtaining seed cells from the culture colonies and repeating the cycle on fresh culture media. In another preferred aspect, such PGC culture process can be interrupted by a cryopreservation step, followed by thawing of the totipotent cells and continuing with a new culture cycle on fresh culture media. Such culture media may also include basic stem cell media or other growth factors. For example, the media may also include LIF, MSCF or bFGF. Although the presence of PSCF is preferred for culturing porcine totipotent cell lines, once a porcine totipotent cell line is established from PGCs less growth factors may be needed to maintain the cell line in culture. Under such circumstances, for example, mouse stem cell culture media may suffice to maintain such cultures. Examples of mouse stem cell culture media are set forth in U.S. Pat. No. 5,453,357.

A still further object of the present invention is to produce a chimeric embryo which is made by using such a totipotent cell line to inject the embryo and to produce a chimeric animal derived from the chimeric embryo.

In yet another aspect, an object of the present invention is to provide a totipotent porcine cell line into which has been introduced at least one extraneous gene, or which has a native gene deleted, knocked out or modified and to produce therefrom a chimeric embryo which is made using the totipotent cell line to provide an animal with a chimeric germ line which is derived from the chimeric embryo and which will result in chimeric animal offspring with the genetically modified trait that is derived from the genetically modified porcine totipotent cells.

It is still another object of the present invention to provide an embryo with a transplanted nucleus which is made by transplanting the nucleus from one or more of the porcine totipotent cells (which are unmodifed cells or have been modified by the introduction of at least one extraneous gene, the deletion or deactivation of a native gene, or the modification of a native gene) into an enucleated porcine ooplasm (or enucleated embryo) and to provide an animal which was derived from the ooplasm or embryo into which the nucleus was transplanted.

DETAILED DESCRIPTION OF THE INVENTION

The PGCs of mammals (such as mice and domestic animals) appear as cells with high alkali phosphatase activity (ALP activity) in the mesodermic cell layer and endodermic cell layer at the base of the allantoic sac outside the embryo. Passive migration of the developing germ cells results from two factors: dynamic morphological formation of the embryo and dynamic cell movement of the PGCs as they migrate. During such migration, PGCs move to the reproductive anlage (conceptacle, genital ridge) which is derived from the mesenchymal cells of the mesentery from the epidermis of the hind gut.

One means for identifying such PGCs in the developing embryo or in culture media is by using ALP activation as an indicator. Literature is sketchy and unclear with regard to the porcine PGCs migratory path cell counts as correlated with the age of the fetus at various stages of development. PGCs are first observed near the backbone at a fetal age of about 17 days (J. L. Black & B. H. Erikson. Anat. Rec 161, 45–46, 1968), and the genital ridge has been confirmed at a fetal age of about 23 to 24 days. The sex of the embryo can be determined at a porcine fetal age of about 26 days.

Alkaline phosphatase staining can be carried out as described by Matsui et al., Nature 1991 353(6346):750–752. After staining, AP positive cells can be counted using an inverted microscope. Such procedures for identifying PGCs use the mouse monoclonal antibody SSEA-1. In general, PGCs cultures are washed twice with PBS containing 2% calf serum, 0.1% sodium azide and then incubated with the SSEA-1 antibody (1:100 dilution) on ice for about 30 minutes. After washing with PBS, cells are then incubated for about 30 minutes with FITC-conjugated F(ab')$_2$ fragment of goat anti-mouse IgG (H+L) (Cappell, 1:5 dilution). After washing in PBS, cells are fixed in 4% paraformaldehyde before staining for AP.

The term "embryonic ectoderm" is used herein. "Embryonic ectoderm" and "epiblast" can be used interchangeably to refer to the same cell type.

A "primordial germ cell" or PGC as referred to herein means cells (such as obtained from an embryo) which are characterized by their morphology as having large nucleus, high nuclei-cytoplasm-ratio, occasional blebbing and by clearly visible pseudopodia.

A "totipotent cell line" 'or "embryonic stem cell line" or "primordial germ cell line" as used herein means a cell line which can be maintained in long-term culture via passaging (for example more than 40 days) without losing its totipotent capability, in that cells from the cell line can give rise to many differentiated cell types in an embryo or adult, including the germ cells (sperm and eggs). This cell type may also referred to as an "ES cell", an "EG cell" or a "PG cell (PGC)" herein.

A "fibroblast growth factor" (FGF) as used herein means any suitable FGF. More than seven FGFs are known to date. Such FGFs include FGF-1 (acidic fibroblast growth factor), FGF-2 (basic fibroblast growth factor), FGF-3 (int-2), FGF-4 (hst/K-FGF), FGF-5, FGF-6, FGF-7. Each of the suitable factors can be utilized directly in the methods taught herein to aid in the production or maintenance of porcine PGCs or a porcine totipotent cell line derived from PGCs. Each FGF can be screened in the methods described herein to determine if the FGF is suitable to enhance the growth of or allow continued proliferation of such totipotent cells.

"Porcine Stem Factor" (PSCF) or "porcine steel factor" is used herein. Also the corresponding mouse factors are discussed as being "mouse stem factor" (mSCF) or "mouse steel factor". pSCF is also called porcine mast cell growth factor and porcine c-kit ligand in the art. Each of the native SFs has a transmembrane polypeptide, a cytoplasmic domain and an extracellular domain. Soluble pSCF or mSCF refer to a fragment cleaved from the extracellular domain at a specific proteolytic cleavage site. Membrane associated SF refers to both normal SF before it has been cleaved or the SF which has been altered so that proteolytic cleavage cannot take place. The PSCF may be either a soluble form as described in U.S. Pat. No. 5,589,582, or its equivalents, or may be a membrane-bound form, preferably bound on to the surface of a cell.

Feeder cells which produce membrane-bound and/or soluble PSCF may be referred to above and hereinafter as "STO5" or "STO8" and feeder cells which produce MSCF may be referred to as STO cells (the STO cell line is a thioguanine/oubain resistant sub-line of SIM mouse fibroblasts, Wax and Axelrad, Virology 50:339 (1972); STO cells are described in U.S. Pat. No. 5,453,357). The STO5 and STO8 feeder cells are STO cells that have been transfected with a membrane-bound portion (or portions) which encode an active PSCF polypeptide. The full-length sequence for PSCF (SEQ ID NO:2) based on native cDNA (SEQ ID NO:1) and (FIG. 3 attached hereto) is reported in Biology of Reproduction 50:95–102 (1994), and active forms can be produced by transfecting cells with active fragments of the cDNA sequence which may have the polynucleotides encoding the leader sequence amino acids (–25 to –1) removed. Soluble forms preferably omit the polynucleotide transmembrane portion. Additionally, an active form of pSCF can be produced and utilized to transfect STO cells by removing exon 6 from the full length cDNA and substituting a polynucleotide segment that encodes one or more amino acids.

As described above, to express the membrane form of porcine stem cell factor (PSCF) in the mouse fetal fibroblast feeder cell line STO and to provide STO5 or STO8 cell lines or the equivalent, the STO cells may be transfected with a portion of the cDNA encoding the pSCF gene. Alternatively, by eliminating the membrane-binding portion (portion corresponding to nucleotides 715 to 783 of the full length cDNA), the soluble form of pSCF may be produced by STO cells or the like transfected with the polynucleotide encoding the soluble PSCF polypeptide.

For example, STO8 cells are produced by transfecting STO cells with a polynucleotide sequence corresponding to the full-length cDNA in which: (1) the first 70 polynucleotides are removed, (2) exon 6 is excised (polynucleotides 591 to 654) from the full polynucleotide sequence, (3) the excised exon 6 segment is replaced by a three-nucleotide segment encoding the amino acid "Gly", and (4) the fifteen-nucleotide C-terminal tail (polynucleotides 938–952) is removed and replaced by the six-polynucleotide segment 5'-TCTAGA-3'.

Other active PSCF polynucleotides may be utilized. A polynucleotide sequence for an active soluble form of PSCF is reported in U.S. Pat. No. 5,589,582.

The above mentioned documents that relate to various forms of PSCF are all incorporated herein by reference.

PGCs can be extracted from swine fetuses during about 17 to 39 days post fertilization of the embryo. Preferably, 27 day old fetuses are utilized and PGC suspensions are prepared by trypsin (or EDTA) treatment of genital ridges from the porcine embryos (crossbred) and then seeded on feeder cells (for example in 4-well dishes). The feeder cells are mitotically inactivated and may be STO cells that express MSCF or STO transfected cells (e.g., STO5 or STO8 cells) which express PSCF. Examples of cell culture media that may be utilized in addition to such feeder cells or to supplement such feeder cells can be ES medium (Robertson, 1987; *Terato-carcinomas and Embryonic Stem Cells*, IRL Press) supplemented with 15% FCS; the ES medium supplemented with growth factors such as LIF or LIF plus bFGF. Further a conditioned media prepared from 5637 carcinoma call lines may be utilized for initial culturing of PGCs.

Seeded PGC Cultures may be maintained at around 37° C. in 5% $CO_2$ in air. PGCs can be identified by alkaline phosphatase (AP) activity at 1, 3 and 5 days (for example, or at other intervals) using the general procedures set forth above and can also be counted to determine the rate of proliferation. Ideally the cultured PGCs are trypsinized, rinsed with fresh medium (such as PBS or ES media) and re-passaged every 5 to 10 days (preferably every 6 or 7 days), but significantly older live cultures obtained from PGCs which have stopped proliferating may be transferred to media containing LIF and PSCF (preferably PSCF is provided by feeder cells) and begin to proliferate. Depending upon the type and quality of tissue utilized for initial culturing, an un-supplemented gelatin plate may be used. While the first passage of cells resulting from PGCs may be cultured on all of the above media, the best results are obtained with media comprising PSCF and LIF (optionally including bFGF).

In a preferred embodiment, PSCs are cultured in the presence of pSCF (such as pSCF produced by STO8 cells or their equivalent as described above) and LIF (optionally including bFGF) in order to provide long-term cultures of undifferentiated PGCs or undifferentiated totipotent cells resulting from PGCs. When cultured in such a manner porcine totipotent cells maintain their totipotency after more than 6 passages and even after having been maintained via passages for more than 90 days. Such is significant since totipotency is frequently lost in long-term cultured porcine totipotent cells, in particular cell lines older than 40 days. Further, cryopreserved porcine totipotent cells that have been cultured in accordance with the present invention may be thawed and reused in that they retain their totipotency and can be passaged again while maintaining their totipotency.

In preparing the embryonic tissue for the initial culture, it may be desirable to rinse the tissue with media such as the ES medium or PBS medium that does not contain bivalent metal ions such as Mg++ or Ca++. The trypsin solution can contain EDTA at about 0.5 percent and the amount of trypsin in the solution is preferably from about 0.1 to about 0.5 percent, and more preferably is about 0.25 percent. Further rinses with other tissue preparation media utilizing procedures know in the mouse art may be performed, such as with buffered fetal calf serum, and the cells may be recovered from such procedures via centrifugation or precipitation/settling.

The following non-limiting examples are provided to better exemplify the invention.

EXAMPLE 1

Preparation of STO8 Feeder Cells or Similar Feeder Cell Lines

A membrane-bound form of porcine stem cell factor is obtained by utilizing the STO cell line, which is a thioguanine/oubain resistant sub-line of SIM mouse fibroblasts, Virology 50:339 (1972); STO cells as described in U.S. Pat. No. 5,453,357). The STO cells are transfected with a membrane-bound portion which encodes an active PSCF polypeptide. The full-length sequence for PSCF (SEQ ID NO:2) based on native cDNA (SEQ ID NO:1) is reported in Biology of Reproduction 50: 95–102 (1994) (see also, FIG. 3, attached hereto), and an active form is produced by transfecting STO cells with active fragments of the cDNA coding sequence from which the polynucleotides encoding the leader sequence amino acids (–25 to –1) are removed and exon 6 polynucleotides are replaced with a tri-nucleotide fragment encoding the amino acid "Gly".

The following general procedure is followed. RNA is isolated from pig bone marrow stromal cells, RT-PCR is performed utilizing 1 $\mu$g total RNA in 6 $\mu$l $H_2O$ which is incubated at 65° C. for 3 minutes, then chilled on ice. Then added is 4 μl 5×RT buffer, 2 μl 0.1 M Dithiothreitol (DTT), 1 μl RNasin (Promega, Madison, Wiss.), 2 μl 30 μM oligo dT$_{16}$, 2 μl dNTPs (10 mM each DATP, dTTP, dGTP, dCTP), 2 μl 1 mg/ml BSA, 1 μl reverse transcriptase (Gibco Life Technologies, Baltimore, Md.) and the reaction mixture is incubated at room temperature for 10 min., 42° C. for 60 min. 90° C. for 5 min. Then added is 1μ RNase H (4 units, Gibco Life Technologies, Baltimore, Md.) and the reaction is incubated at 37° C. for 20 min. prior to Sephadex™ G-50 column chromatography to purify the cDNA product. The cDNA product is subjected to PCR using the oligonucleotides 5'MSFHindIII (5'GGT CAA GCT TCG CTG CCT TTC CTT ATG AAG AAG, SEQ ID NO: 3) and 3'MSFXbaI (5'TCC ATC TAG AAC CAC CCA ATG TAC GAA AGC AAC, SEQ ID. NO: 4). SEQ ID NO: 1 contains a HindIII site and includes nucleotides 1–24 of SEQ ID NO: 3 (SEQ ID. NO:5 in this application) of U.S. Pat. No. 5,589,582). SEQ ID. NO: 4 contains an XbaI site and the reverse complement of nucleotides 915 through 935 of LO7786. The resulting PCR product is cleaved with HindIII and XbaI and cloned in pRcCMV (Invitrogen, Portland, Oreg.). The resulting plasmid is described as pSCFpRcCMV#2 and contains the full-length porcine cDNA for stem cell factor.

Xba and StuI are used to cleave pSCFpRcCMV#2 and a DNA fragment of approximately 250 bp (fragment 1) is isolated. ClaI and XbaI are also used to cleave pSCFpRcCMV and a DNA fragment of approximately 6.2 Kb is isolated (fragment 2). Two oligonucleotides described as 5'SCFlk (ATCCATCGAT GCCTTCAAGG ATTTGGAGAT GGTGGCACCT AAAACTAGTG AATGTGTGAT TTCTTCAA, SEQ ID NO:6) and 3'SCFlk (TCT GAGGCCTTCC TATTACTCT ACTGCTGTCA TTCCCTTTTT CAGGAGTTAA TGTTGAAGAA ATC, SEQ ID NO:7) are synthesized. The oligonucleotides (1 μg (10 μg) of SEQ ID NO: 6 and (1 μg 10 μl) of SEQ ID NO: 7 are mixed with 3 μl 10X Klenow buffer [Sambrook, 1989 #1973] and incubated at 75° C. for 5 min. and then allowed to cool slowly. Afterwards 2 μl 2.5 mM each dXTP, 1.5 μl (7.5 unit) DNA polymerase Klenow fragment 3.5 μl H2O are added. After 30 min at 37° C., the reaction is heated at 70° C. for 10 min. The DNA fragment (fragment 3) is cleaved with ClaI and StuI. A three-way ligation is then performed with the DNA fragments 1,2 and 3. A resulting plasmid ppSCF is identified to have the correct sequence, shown in FIG. 6 (SEQ ID NO: 8 encoding amino acid sequence SEQ ID. NO: 9). The plasmid does not contain exon 6 and therefore is a form of SCF that is ordinarily expressed preferentially as a membrane bound form.

STO cells are electroporated according to the BIORAD (Hercules, Calif.) instructions for use of the Gene Pulser® Electroprotocols, using PvuI linerized PpSCF. Cells are selected for growth in G418 (500 μg/ml) and analyzed for the expression of the modified pSCF, using RT-PCR from RNA isolated from G418 resistant clones. Examples of STO cell lines that are successfully transfected with the polynucleotides of the above plasmid are designated as cell lines STO5, STO8, STO12 and STO18.

STO cell (or other STO type cell lines such as STO8) were used as feeder cells. The STO8 cells express the membrane-bound form of porcine SCF. The feeder cells were maintained in Dulbecco's modified Eagle's medium (DNEM; Life Technologies) supplemented with 10% fetal calf serum (FCS, Boehringer Mannheim) 100 μg/ml streptomycin sulfate and 100 IU/ml penicillin G at 37° C. with 5% $CO_2$ in air. The preparation of STO feeder layers is described elsewhere (Robertson, 1987). Briefly, confluent monolayers of feeder cells were treated with 5 μg/ml mitomycin C for 2.5 h and seeded onto gelatine-coated 4-well-dishes (Nunc; 1.5×10$_6$ cells per well) for proliferation studies of PGCs in 5 days of culture and 35 mm petri dishs (6×10$_6$ cells per dish) for study of prolonged culture of porcine PGCs and were used within 24 hours.

Figure 5:
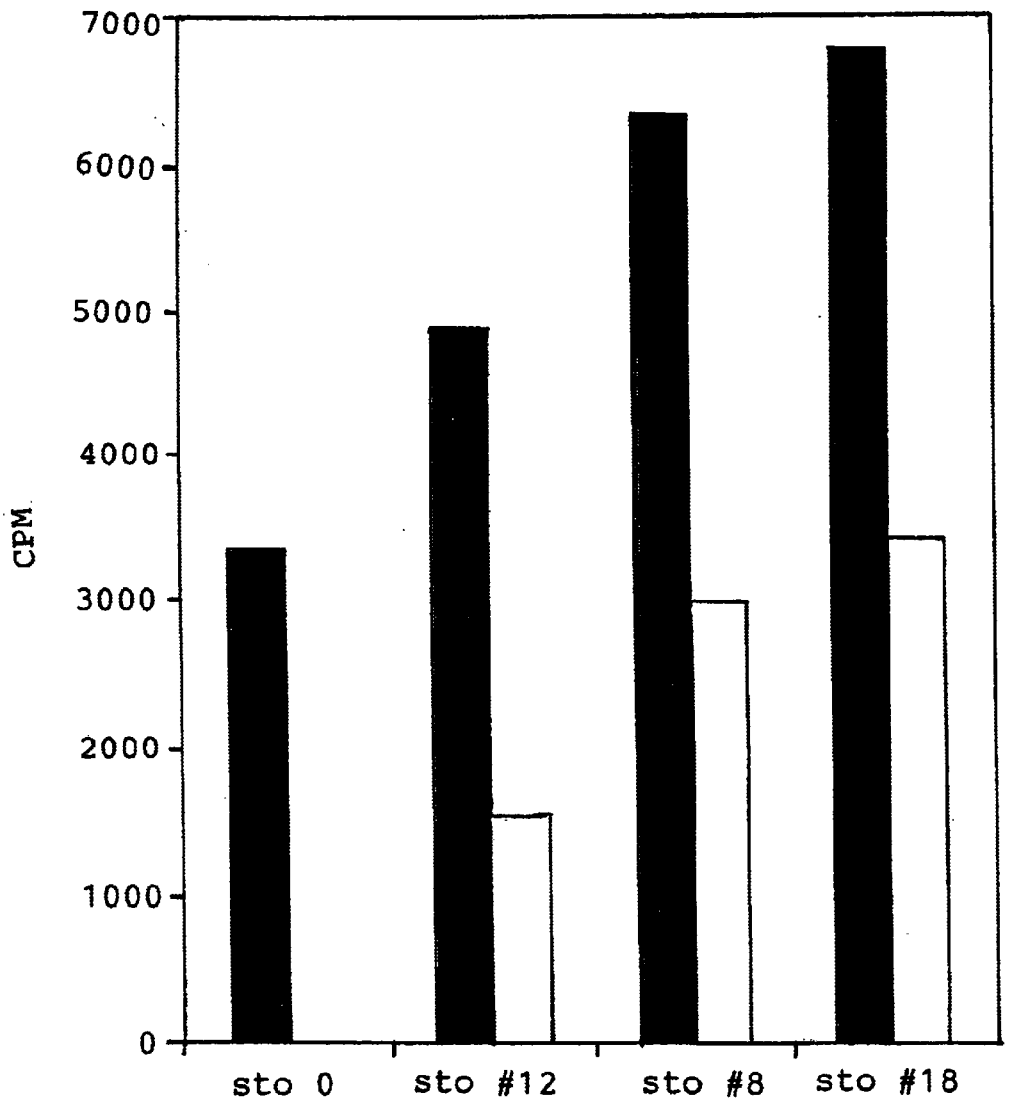
FIG. 5 shows a comparison of proliferation results for pig bone marrow cells cultured in the presence of STO cells as compared to STO cells transfected with the polynucleotide sequence that is set forth in FIG. 6. The proliferation results for pig bone marrow cells cultured in the presence of the transfected cells are significantly better than results with regular STO cells.

Cells (STO (control expressing murine membrane SCF), STO8, STO12 and STO18) are plated into 96 well flat bottom plates in Iscove's Modified Dulbecco's Media containing 10% heat-inactivated fetal bovine serum. Prior to the addition of bone marrow cells, the plates are irradiated to prevent further proliferation of the STO, STO5, STO8, STO12, and STO18 cells. Bone marrow cells are added to the wells. After 2 days in culture, 1 microcurie of $^3$H-Tdr is added to each well, and the plates are harvested on day 3. Results are counts per minute (cpm) and expressed as a mean value of triplicate plates. FIG. 5 shows that each of the transfected STO cell lines supports the proliferation of pig bone marrow cells to a greater extent than the untransfected STO cell line. The proliferative response on the bone marrow cells of the transfected cells is similar to that observed with untransfected STO cells that were cultured in combination with of 100–200 μg soluble pig SCF (for example, as set forth in U.S. Pat. No. 5,589,582).

EXAMPLE 2
Short-Term Culture of Porcine Primordial Germ Cells

To establish primordial germ cell-derived porcine embryonic germ (EG) cells, optimal culture conditions are important. The ability for four types of culture media and two feeder cell types to support porcine primordial germ cell (PGC) proliferation in primary culture was conducted as follows. Cells were cultured in: ES medium (Robertson, 1987; *Teratocarcinomas and Embryonic Stem Cells*, IRL Press) (control) that is supplemented with 15% FCS; ES medium supplemented with the growth factor LIF; and ES medium supplemented with the growth factors LIF and bFGF; and a conditioned medium prepared from 5637 carcinoma call lines. Feeder cells which are mitotically inactivated STO and STO8 cells were seeded in 4-well-dishes.

PGC suspensions were prepared by trypsin treatment of genital ridges from 27 day old embryos (crossbred) and then seeded on feeder cells. In particular, urogenital ridges of the fetuses were collected in PBS supplemented with 10% FCS and washed two times in PBS. The genital ridges were incubated in digestive solution (0.1% trypsin/0.05% EDTA) at 37° C. for. 5–8 min and dissociated by gentle pipetting. Suspension of PGCs and somatic cells was seeded in aliquot equivalents of one tenth of a genital ridge per well in 4-well-dishes (Nunc) onto feeder cells. The cells were cultured in embryonic stem cell (ESC) medium consisting of DMEM, supplemented with 15% FCS, 2 mM L-glutamine (Gibco, Life Technologies), 10$^4$ mM β-mercaptoethanol (Sigma), 2 mM non-essential amino acids (Gibco, Life Technologies) 100 μg/ml streptomycin sulfate and 100 IU/ml penicillin G in 5% $CO_2$ in air at 37° C. ES medium was supplemented with murine leukemia inhibitory factor (ESGRO, Amrad, 1000 IU/ml) alone or in combination with human basic fibroblast growth factor (Sigma, 10 ng/ml). The medium was changed every other day. Cultures were maintained at 37° C. in 5% $CO_2$ in air.

Figure 7A:
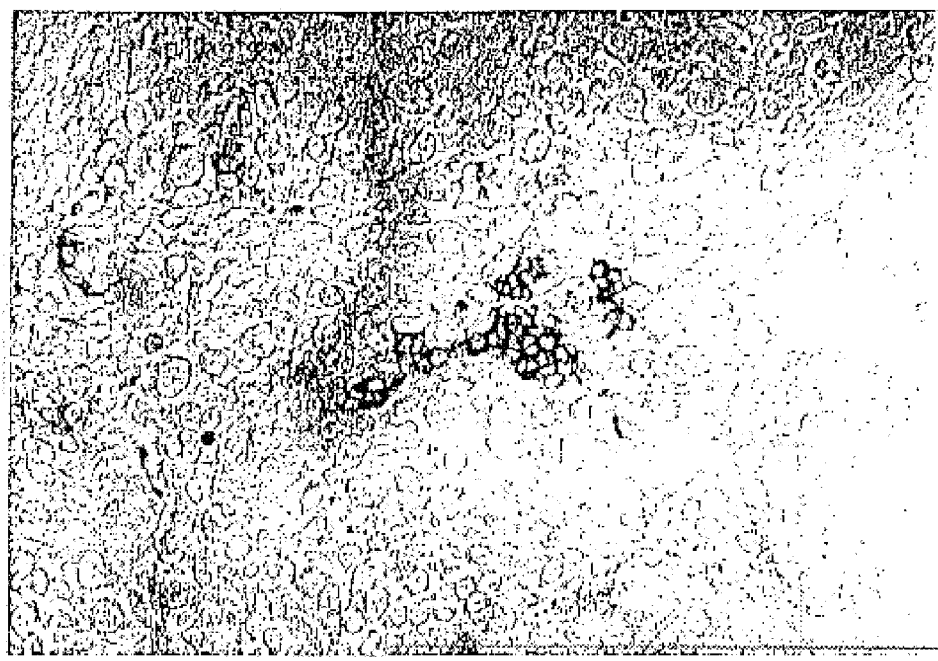
FIGS. 7A–7C illustrate the proliferation of porcine PGCs isolated from 27 day old fetuses. PGCs are cultured in ES medium supplemented with LIF on STO8 cells.
Figure 7B:
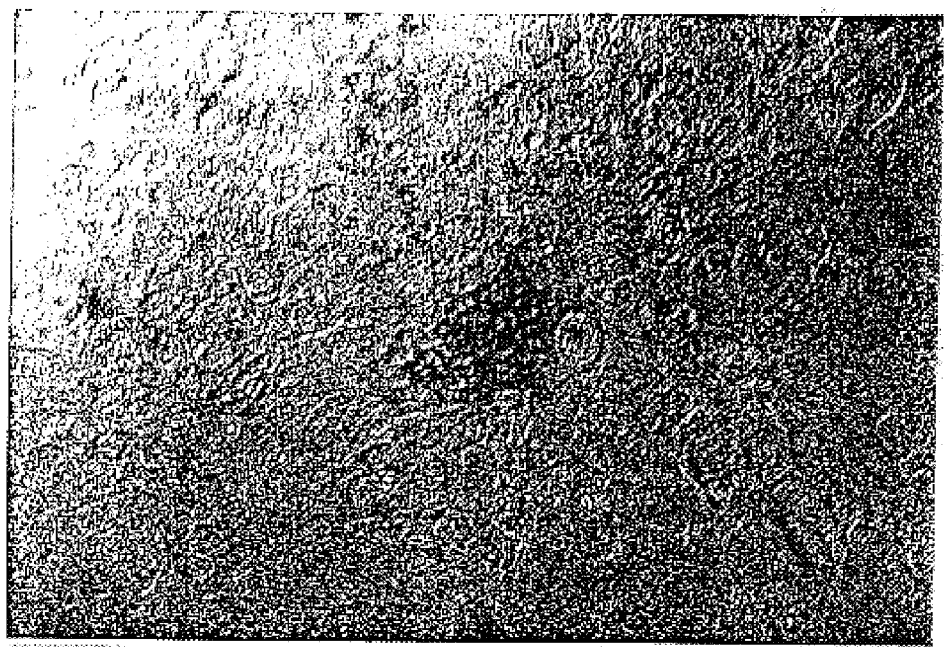
Figure 7C:
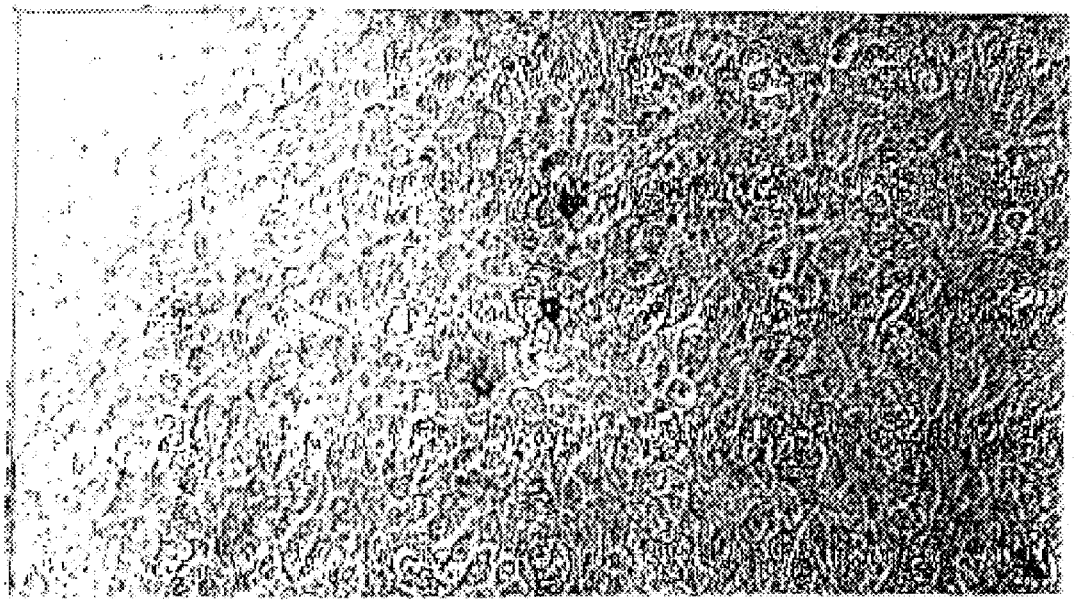

PGCs were identified by alkaline phosphatase (AP) activity at 1, 3 and 5 days and counted. In determining the number in culture, cells were fixed by drying in air and stained with Alkaline Phosphatase Leukocyte Kit (Sigma) according to the manufacturer's instructions. AP-positive cells in 4 well dishes were counted using an inverted microscope. Alkaline phosphatase (AP) activity was used for identification of porcine PGCs after different days of culture. Initially, PGCs were identified in culture as single red AP-positive cells which eventually formed groups of small colonies by aggregation (FIG. 7A). The increase in the PGC number within 3 days of culture correlated with the formation of discrete colonies containing up to 20 cells and eventually continued to grow over 5 days of culture period (FIGS. 7B and 7C). Each of the culture conditions were provided in triplicate to verify results and the results reported were averages of cell counts from the three sets of data for each culture condition.

Figure 9A:
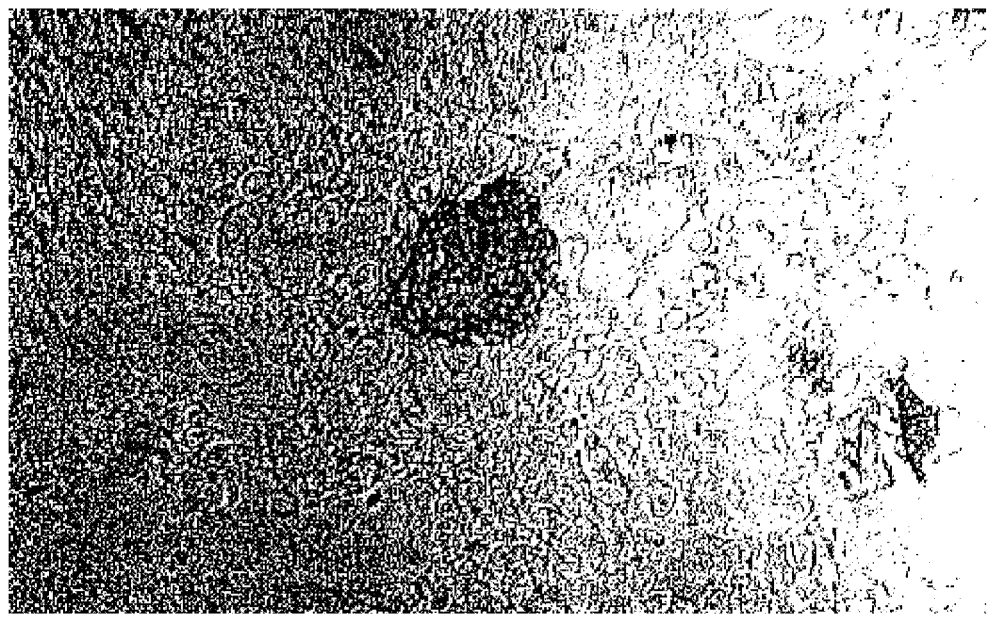
FIGS. 9A and 9B are photographs of PGC cultures after 8 days of culturing on STO8 feeder cells in the presence of LIF. PGCs are stained to identified by AP activity.
Figure 9B:
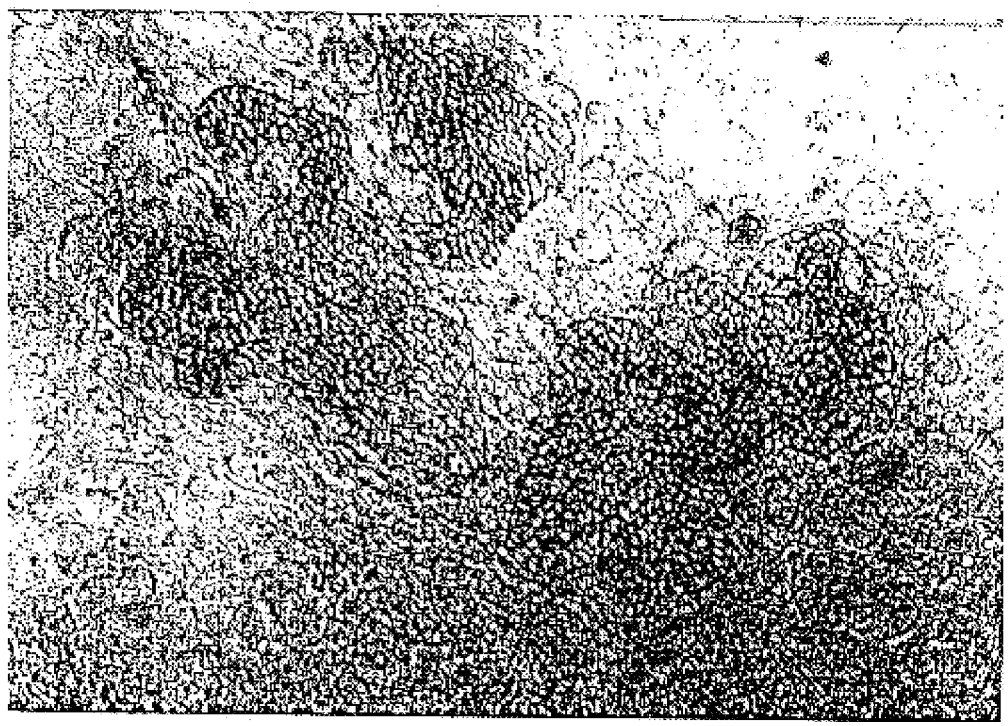

Results of culturing PGCs for 8 days on STO8 feeder cells in the presence of LIF are shown graphically in FIGS. 9A and 9B. PGCs were identified by AP activity. Some colonies have become multilayered (9A) and however, some colonies were growing as a monolayer on STO8 cells and contained only a small number of strongly stained cells together with AP negative cells (9B).

Figure 2:
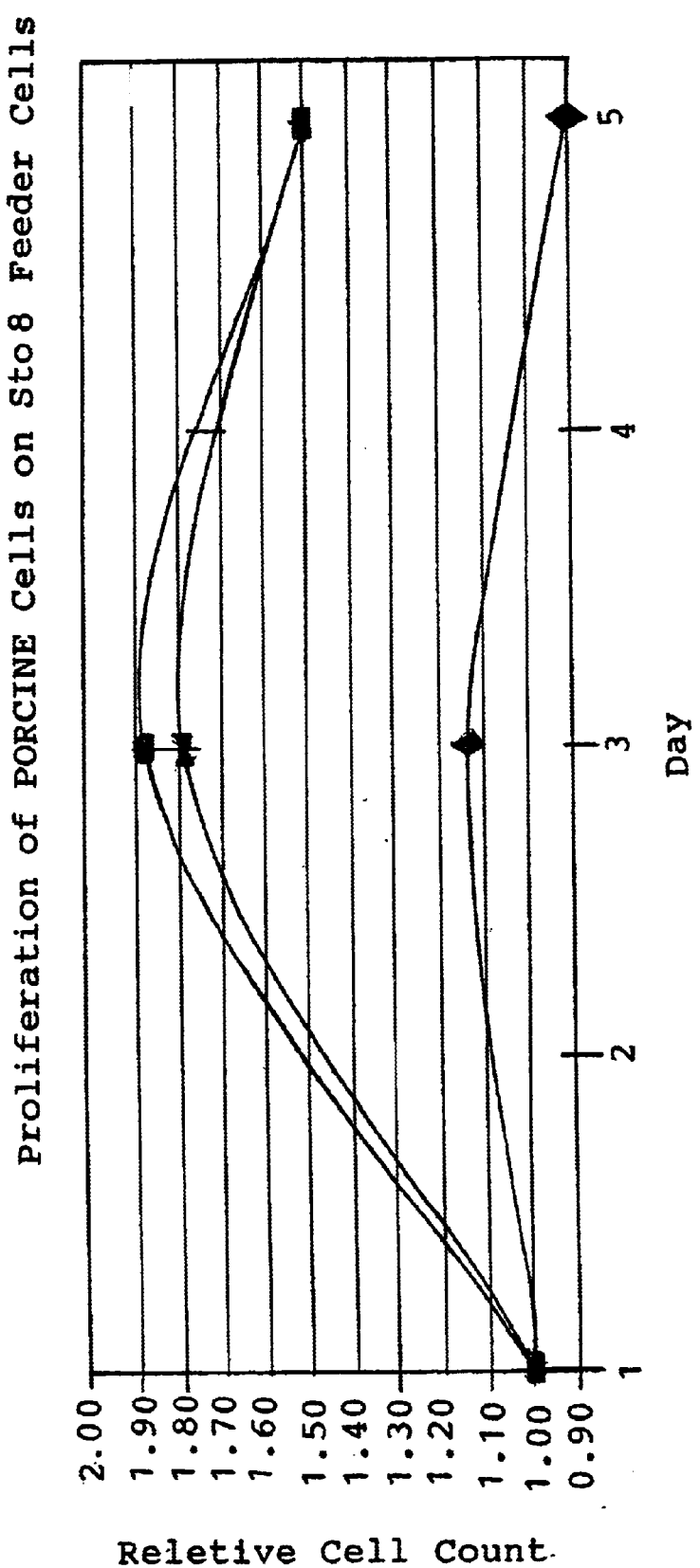
FIG. 2 illustrates the number of PGCs (relative to the number of PGCs present on the first day) in non-passaged initial cultures on days 1, 3 and 5 days when cultured on STO8 feeder cells (producing a form of membrane-bound pSCF) in three out of four different culture media. The three plot lines represent three out of the four different culture conditions used: (1) ES medium (control) that is supplemented with 15% FCS (ES), (2) ES medium supplemented with growth factors LIF (ES+LIF), (3) ES medium supplemented with LIF plus bFGF (ES+JIF+bFGF) and (3) conditioned medium prepared from carcinoma cell line 5637.

FIGS. 1 and 2 show the relative number of PGCs on 1, 3, and 5 days in culture utilizing STO feeder cells and STO8 feeder cells, respectively, (FIG. 1 data reports results with STO feeder cells with membrane-bound MSCF, and FIG. 2 data reports results with STO8 feeder cells with membrane-bound pSCF excluding the polypeptides corresponding to exon 6). The three plot lines in each Figure represent three of the four different culture media utilized with the respective feeder cells under the same culturing conditions. The plot line corresponding to the ES medium control utilizes just the feeder cells and the ES medium described above.

One of the plot lines in FIG. 1 shows the relative numbers of PGCs resulting from culturing in the presence of STO feeder cells and the 5637 carcinoma cells medium. Although, the 5637 carcinoma cell medium supports cell proliferation well for first three days, the total number of cells decreases rapidly after day three. The results for the first three days in FIG. 1 show that the STO feeder cell support initial growth better than the results in FIG. 2 from STO8 for the first 3 days with regard to the 5637 carcinoma cell conditioned medium. As demonstrated by a comparison of FIG. 2 with FIG. 1, the numbers of PGCs resulting from culturing in the presence of the STO8 cells is better for the other three types of media than for the same three types of media in the presence of STO cells. Thus, for first passage of PSC culturing, the proliferation of PGCs is significantly better on STO8 feeder cells than on STO feeder cells for each of the four media types except the carcinoma cell 5637 media.

The success of STO8 in the production of porcine membrane bound stem cell factor (SCF) is significant. The importance of mouse membrane bound SCF (MSCF, from STO cells) for the viability and growth of mouse PGCs has been published (Matsui et al. 1992). Until now it was not clear that porcine SCF (pSCF) would act in a similar manner to provide totipotent porcine cells.

The data plotted in FIGS. 1 and 2 are displayed in Tables 1 and 2 along with some simple statistical analysis. The first two columns in each table are the culture day and culture conditions. The fourth column is the sample standard deviation (SD) with a population of four (n=4). The last column is the percent relative standard deviation (% RDS) and the average given at the bottom is the average of the % RDS value on day 3 and 5.

Table 1 is presented below to provide the results with STO feeder cells. Day 1 SD and % RDS are zero because the data was normalized to Day 1.

TABLE 1

| DAY | MEDIA | AVERAGE | SD | % RDS |
|---|---|---|---|---|
| 1 | ES | 1.00 | 0.00 | 0.000 |
|   | 5637 | 1.00 | 0.00 | 0.000 |
|   | ES + LIF | 1.00 | 0.00 | 0.000 |
|   | ES + LIF + bFGF | 1.00 | 0.00 | 0.000 |
| 3 | ES | 1.12 | 0.16 | 14% |
|   | 5637 | 1.81 | 0.35 | 19% |
|   | ES + LIF | 1.29 | 0.43 | 33% |
|   | ES + LIF + bFGF | 1.10 | 0.13 | 12% |
| 5 | ES | 1.06 | 0.15 | 14% |
|   | 5637 | 1.38 | 0.24 | 18% |
|   | ES + LIF | 1.32 | 0.27 | 20% |
|   | ES + LIF + bFGF | 1.30 | 0.18 | 6% |
|   | AVERAGE |  |  | 17% |

Table 2 is presented below to provide the results with STO8 feeder cells. Day 1 SD and % RDS are zero because the data was normalized to Day 1. The other aspects of the data are the same as reported above for the results in Table 1.

TABLE 2

| DAY | MEDIA | AVERAGE | SD | % RDS |
|---|---|---|---|---|
| 1 | ES | 1.00 | 0.00 | 0.000 |
|   | 5637 | 1.00 | 0.00 | 0.000 |
|   | ES + LIF | 1.00 | 0.00 | 0.000 |
|   | ES + LIF + bFGF | 1.00 | 0.00 | 0.000 |
| 3 | ES | 1.14 | 0.17 | 15% |
|   | 5637 | 1.87 | 0.52 | 20% |
|   | ES + LIF | 1.96 | 0.34 | 18% |
|   | ES + LIF + bFGF | 1.76 | 0.54 | 30% |
| 5 | ES | 0.91 | 0.15 | 14% |
|   | 5637 | 1.51 | 0.37 | 20% |
|   | ES + LIF | 1.69 | 0.22 | 13% |
|   | ES + LIF + bFGF | 1.51 | 0.10 | 7% |
|   | AVERAGE |  |  | 19% |

Considering the SD information along with the simple cell count, the data shows clearly that for initial PSCs cultures proliferation is significantly better on STO8 than on STO for all conditions except 5637. In the case of 5637 media, the results are not significantly different between the two feeder cells.

One explanation for the similarity in the 5637 on STO and the STO8 results may very well be that 5637 conditioning medium may contain additional other growth factor(s), which are as of now undefined that also support the initial proliferation of PGCs on the STO feeder cells. Further, adequate growth factors may remain in the tissue or in the seed cells themselves that have an effect upon growth during the first three days.

Figure 8:
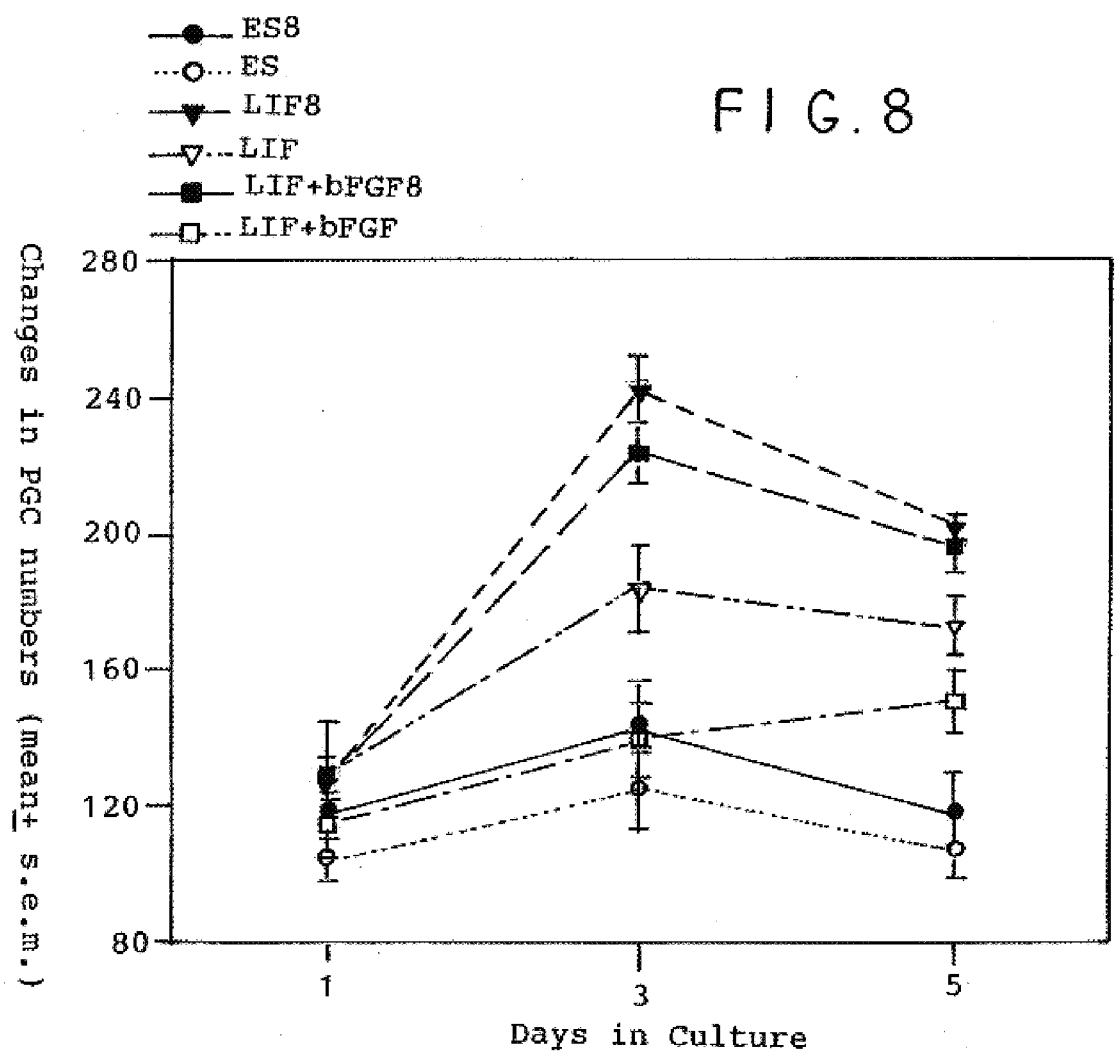
FIG. 8 shows data from a comparison of STO and STO8 cells when they are used as feeder cells. PGCs were cultured in ESC medium without added growth factors on STO cells (open circles) or STOB cells (closed circles), with LIF on STO cells (open triangles) or (STO8 cells (closed triangles), or with LIF plus bFGF on STO cells (open squares) or STO8 (closed squares). Data are shown as the mean±s.e.m.

The results of this experiment are shown in FIG. 8. Data are plotted in as mean±s.e.m values as shown graphically in FIG. 8. PGCs were cultured in ESC medium without added growth factors on STO cells (open circles) or STO8 cells (closed circles), with LIF on STO cells (open triangles) or (STO8 cells (closed triangles), or with Lif plus bFGF on STO cells (open squares) or STO8 (closed squares). The values obtained for the membrane-bound form of porcine SCF and mouse SCF are significantly different (p<0.05) on day 1. Values obtained for the membrane-bound form of porcine SCF with LIF and SCF alone are significantly different (p<0.01) on day 3; and (p<0.001) on day 5.

EXAMPLE 3
Long-Term Culture of Porcine Primordial Germ Cells

The above culture conditions were repeated for multiple passages. Cells from the first passage were trypsinized and rinsed to obtain seed cells for the second and subsequent passages. (Data not reported). The results have shown that STO8 feeder cells and ES medium supplemented with LIF alone or combination of LIF with bFGF is best for long-term culture of porcine totipotent cells such as porcine PGCs.

Cultures of totipotent cell lines were maintained for more than 6 passages and some more than 90 days via passaging every 6 to 7 days in the presence of STO8 feeder cells and preferably also in the presence of least LIF or LIF and bFGF. Cryopreserved cells from such cultures were reconstituted using methods standard in the art and repassaged. Totipotent cells were obtained from such cryopreserved cells.

Figure 15:
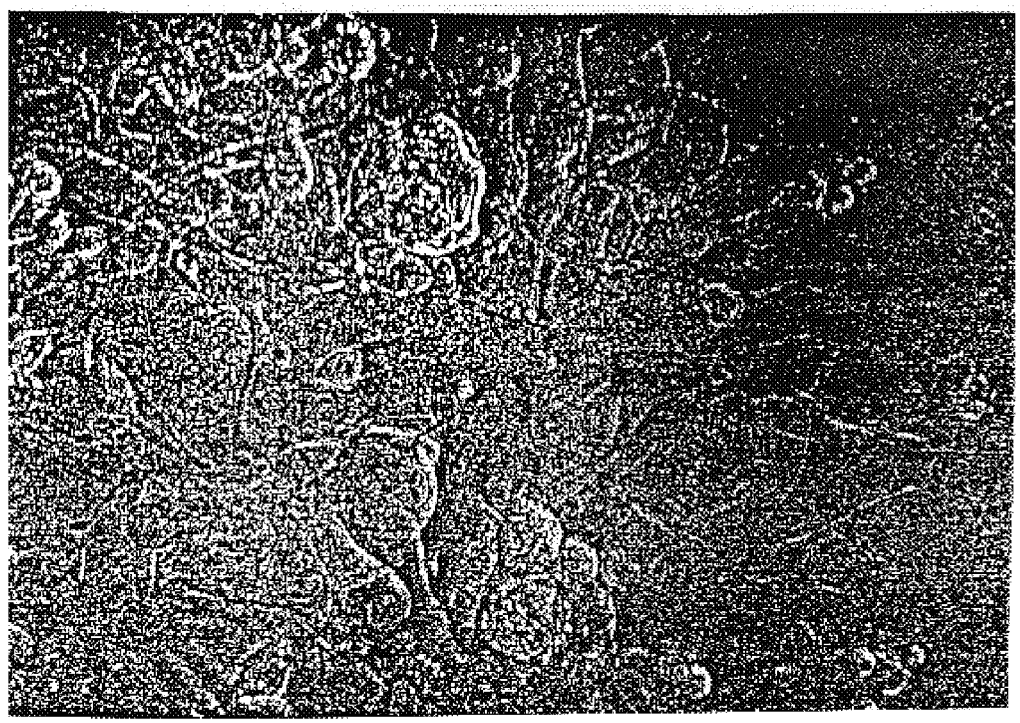
FIG. 15 shows PGC-derived colonies obtained from frozen/thawed PGCs which have been cultured on STO8 feeder cells after their fifth passage. The cells were passaged every two weeks.
Figure 16:
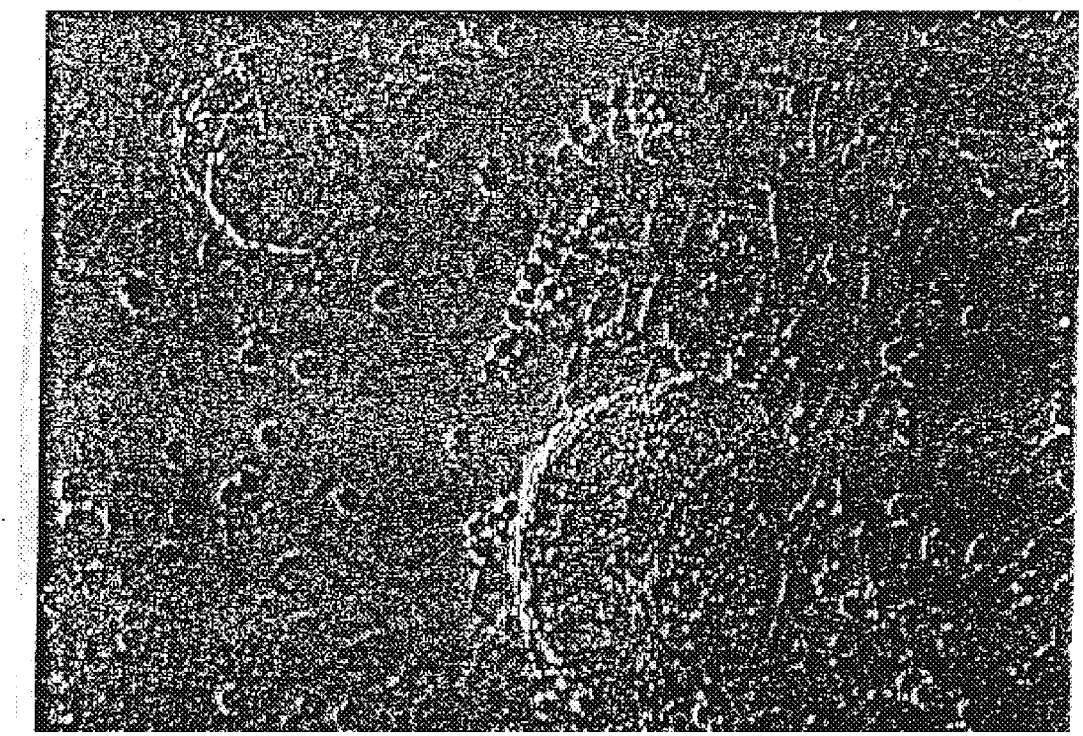
FIG. 16 shows PGC-derived colonies obtained from frozen/thawed PGCs after their fifth passage. The cells were passaged every two weeks.
Figure 23:
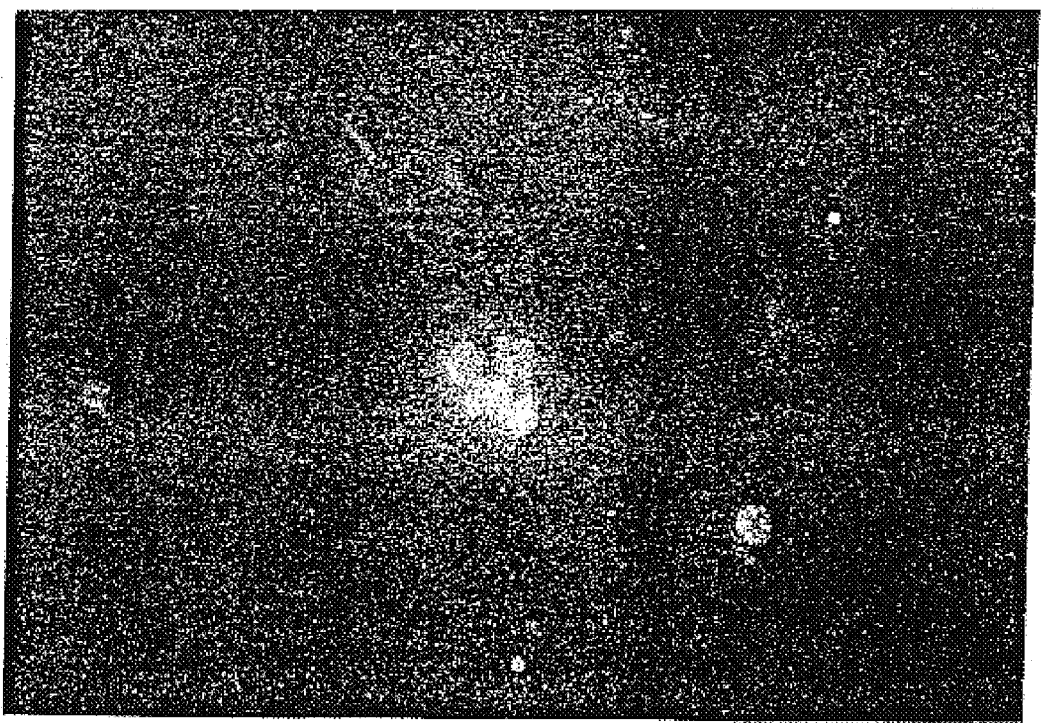
FIG. 23 shows SSEA-1 positive porcine primordial germ cells after having been frozen and thawed and after their fifth passage. The cells were passaged every two weeks.

See FIGS. 15, 16 and 23 for cultures of PGCs resulting from frozen/thawed PGCs.

EXAMPLE 4
Culture of Transgenic Porcine Primordial Germ Cells
Summary of Cultures and Results The procedures from Example 2 were followed utilizing the STO8 feeder cells and initial culture PGCs were obtained from EDTA-treated day 26 genital ridges isolated from fetuses of Duroc-German Landrace crossbred gilts mated with transgenic boars heterozygous for a gene construct consisting of the human growth hormone (GH) gene driven by the murine whey acidic polypeptide (WAP) promoter. Porcine totipotent cell lines having the gene construct were identified using methods standard in the art and established through passaging.

The porcine totipotent cell lines having the gene construct were also maintained in long-term culture for at least three months using the passaging and culture conditions as set forth in Examples 2, above. The cells may be passaged about every 3 days to two weeks but were optimally passaged once every six to seven days by trypsin/EDTA treatment.

Further the porcine totipotent cells lines having the gene construct as described above also survived cryopreservation in liquid nitrogen and proliferated after thawing.

Details of the materials and methods as well as of the individual experiments are as follows:

A. Animals Used
PGC Donors

Eight sows (Duroc/German Landrace/Pietrain-crossbred) were slaughtered at different stages of pregnancy which varied between 25 and 28 days after natural mating. All of them had been hormonally treated by Pregnant Mare's Serum Gonadotropin (PMSG, 1000 IU) followed by Human Chorionic Gonadotropin (HCG, 750 IU) after 72 hours. The females were mated with transgenic boars heterozygous for a gene construct consisting of the human growth hormone (GH) gene driven by the murine whey acidic protein (WAP) promoter. Also five of the dams had this transgenic marker. 119 fetuses were obtained. They were transported to the lab in cold PBS (without $Ca^{++}$, $Mg^{++}$) on ice. Time between slaughtering and beginning of preparation was about 2 hours.

Embryo Donors

Non-transgenic blastocysts were recovered from 26 superovulated (1500 IU PMSG followed by 750 IU HCG after three days) crossbred gilts (German Landrace Pietrain). The animals were slaughtered on day 6 after mating (day of the first mating=day 0).

Recipients

For embryo transfer 12 recipient gilts were used (Duroc or German Landrace). They also were prepared by hormonal stimulation synchronous or 24 hours asynchronous with the donors.

B. Isolation of Transgenic PGCs

In the lab, fetuses were transferred to fresh PBS (without $Ca^{++}$, $Mg^{++}$) at room temperature. Each fetus was dissected by dividing the fetus caudal to the forelimb anlage and the genital ridges were removed from the fetus. In dependence on the age specific stage of development of the genital ridges gonads including or without their surrounding tissues such as mesonephric were removed. Isolated tissues were washed with PBS and treated with 0.02% EDTA solution for 15 to 20 minutes at room temperature. After incubation the gonads were transferred to culture medium and pricked with a fine cannula (30 g) to release the PGCs. After disaggregation and gentle pipetting the suspension was immediately transferred to either gelatin-coated dishes or to STO8 feeder cells which were inactivated by mitomycin C.

C. In vitro Culture of PGCs
Media

For in vitro culture two different media compositions were tested. In the first experiments simple media was used: Dulbecco's Modified Eagle's Medium, DMEM (Sigma) with sodium bicarbonate, without L-glutamine and pyruvate, supplemented with 10% heat inactivated fetal calf serum. The media also contained 1 mM L-glutamine, 1 mM sodium pyruvate (0.1 M) and penicillin (100 U/ml)/streptomycin (0.5 mg/ml) were added.

The further experiments were carried out with Embryonic Stem Cell Medium (ES) according to Robertson (1987) (*Teratocarcinomas and Embryonic Stem Cells*, IRL Press): DMEM containing 15% fetal calf serum, MEM nonessential amino acids (0.1 mM), L-glutamine (1 mM), sodium pyruvate (1 mM), β-mercaptoethanol (0.1 mM) and antibiotics.

In vitro culturing conditions were 37° C., 5% $CO_2$ and saturated air humidity. The culture dishes (Nunc or Falcon) were petri dishes or multidishes (4–6-well-dishes).

Feeder Cells

Cells were seeded on gelatin-coated dishes until micromanipulation. After injection the cells which were not needed were seeded on murine STO cells (STO8) transfected with the membrane-bound pig stem cell factor.

Particular Culture Types
Experiment (i)

The dispersed cells collected from the embryos of the same dam were pooled. Primordial germ cells were injected into host blastocysts on the day of isolation. The following day the cells were seeded on feeder layer.

Experiment (ii)

The isolated PGCs of two pairs of gonads, respectively, were cultured on STO8 cells for 4 days. After four days they were injected into host blastocysts.

Experiment (iii) and (iv)

Recovered PGCs from the isolated gonads were cultured separately on gelatin-coated dishes for up to 24 hours until injection. After manipulation the cells were seeded onto feeder cells.

Experiment (v)

The cells were maintained in long-term culture. After freezing and thawing they were passaged two times and used for microinjection. When the PGCs had been seeded onto feeder cells the medium was changed every other day. Approximately 4 days later the first proliferating primordial germ cells could be seen. After 7 to 10 days in culture the first embryonic stem cell like colonies could be observed. For further subculture the cells were passaged by trypsin/EDTA treatment at 6- to 10-day intervals.

D. Cryopreservation and Thawing Procedures

For cryopreservation the cultivated PGCs were washed with PBS and incubated in 0.25% trypsin-EDTA-solution for up to 3 minutes at 37° C. The cells were suspended in medium and centrifuged at 600×g for 5 minutes. The pellet was resuspended in 1 ml freezing solution consisting of 90% fetal calf serum/10% Dimethylsulfoxide (DMSO) and filled in cryotubes (Nunc). The cryotubes were cooled at −80° C. and stored in liquid nitrogen (LN2) after 24 hours.

Thawing was performed rapidly in a 37° C.-waterbath. Thawed cell-suspension was diluted in 4 ml culture medium and centrifuged at 600×g for 5 minutes. After resuspending the pellet in 1 ml culture medium the cells were seeded onto freshly inactivated STO-cells (STO8).

E. Characterization of Porcine PGCs

Alkaline Phosphatase

Activity for alkaline phosphatase (AP) was demonstrated by using the AP staining kit (Sigma) according to the manufacturer's protocol. AP-staining was carried out in about 2 weeks intervals during the long-term culture. Thawed PGCs also were tested for AP activity.

SSEA-1 Stage Specific Embryonic Antigen-1

For staining with SSEA-1 porcine primordial germ cells were used at different passages (2, 5 and 11 passages) which were cultivated for 4, 10 and 16 weeks, respectively. Also cryopreserved and thawed cells were tested for SSEA-1-activity. One to three days before staining PGCs and feeder cells were transferred on gelatinized cover slips.

Staining of undifferentiated cells with monoclonal antibodies was carried out according to the following protocol:

Cells were rinsed three times with PBS fixation with methanol:acetone (7:3) at −20° C. for 6 mins.

rinsing with PBS three times the fixed cells are incubated with 10% goat serum in a humidified chamber for 30 min at room temperature to prevent unspecific immunostaining incubation with the first antibody SSEA-1 (1:3 in PBS) for 90 min at 37° C.

rinsing with PBS three times incubation with diluted FITC-labeled goat anti-mouse IgG (diluted 1:200 in PBS+0.5% BSA) in a humidified chamber overnight at 4° C.

rinsing with PBS three times rinsing with aqua tridest cover slips are embedded in anti-fade mounting medium and analyzed with the confocal laser microscope (Zeiss)

The following antibodies were used in the assays:

SSEA-1 (polyclonal hybridoma cell supernatant)

Fluorescein (DTAF)-conjugated Affini Pure F(ab')$_2$ Fragment Goat Anti-Mouse IgG (H+L) #115-016-062 Jackson Immuno Research, Disnova, Germany F. Micromanipulation and Transfer of Embryos Non-transgenic recipient embryos were recovered from 26 superovulated German Landrace-Pietrain crossbred gilts. They were slaughtered on day 6 after mating (day of the first mating=day 0). Flushing the uterine horns with warm PBS containing gentamicin (50 mg/1000 ml) at these times provided compacted morula, early blastocyst and fully expanded blastocyst stage embryos.

The embryos were placed in transfer medium (PBS containing 20% heat inactivated lamb serum and gentamicin) covered by liquid paraffin at 39° C. in 5% $CO_2$.

In preparation for injection, a suspension of non-adherent PGCs, collected from the culture dish by using a mouth-controlled glass micropipette was transferred into a drop of micromanipulation medium.

For microinjection the embryos were held in a conventional holding pipette (130–140 µm internal diameter); the injection pipette had about 30 µm internal diameter. Five to ten cells phenotypically resembling PGCs were deposited within the blastocyst cavity.

After injection the embryos were replaced in the incubator for up to 5 hours to check whether they re-expanded.

For transfer 11 recipient gilts were prepared for blastocyst transfer by hormonal stimulation 24 hours asynchronous with the donors. One transfer was carried out in a synchronous recipient. Transfers were performed by endoscopy under general anesthesia. Per recipient 16–20 blastocysts were transferred into the tip of one uterine horn. Five weeks later the recipients were slaughtered to check chimerism.

G. Collection of Fetal Tissues for Analysis and Preparation for PCR-amplification For the rapid detection of transgenic fetuses to use as donors of PGCs DNA was prepared as follows. About 100 mg of liver tissue was lysed in 100 [11 Kawasaki buffer comprising 20 mM Tris-HCl, pH 8.3, 1.5 mM $MgCl_2$, 25 mM KCl, 0.5% (v/v) TWEEN 20 supplemented with 1 mg/ml proteinase K at 64° C. for 4–5 hours. Prior to the PCR reaction, proteinase K was heat inactivated (95° C., 15 min; 2 times) and cell debris was removed by centrifugation (13,000×g, 5 min). The supernatant was diluted 1:5 and for the PCR reaction 5 µl as templates were used.

The fetuses resulting from blastocyst injection were dissected. Ten to eleven different tissue samples were collected separately: whole fetus (skin and muscle), umbilical cord, brain, heart, lungs, gastrointestinal tract, liver, kidney, gonads, fetal placenta, spleen, mesonephron. The samples were incubated at 64° C. overnight in Kawasaki buffer and proteinase K.

PCR-amplification

The PCR reactions were carried out in a final volume of 50 µl using 5 µl of the diluted lysates as templates. Amplifications were performed in 10×PCR buffer (166 mM $(NH_4)_2 SO_4$, 677 mM Tris-HCl, pH 8.8, 0.1% (v/v) TWEEN 20, 20 mM $MgCl_2$), 0.2 mM of each DNTP's, 50 pmol of each primer (PWAP 8 and hGh S2.1) and 1 U Taq polymerase.

The sequences of the primers were 5'-CCA CCC CCA AAG TCT TCC TCC TGT GGG TC-3' (pWAP8, SEQ ID NO:10) and 5'-ATG CGC ACC CAT TCC CCA AG -3' (hGh S2.1, SEQ ID NO:11).

After an initial template denaturation step at 95° C. for 5 min, primer annealing at 68° C. for 40s and primer extension at 72° C. for 40s PCR was carried out for 35 cycles each consisting of 40s denaturation at 95° C., 40s annealing at 68° C. and 40s polymerization at 72° C. in a RoboCyclere (Stratagene). The PCR products were electrophoresed on a 2% agarose gel (1×TBE buffer, 120V const.), stained with ethidium bromide and evaluated using ultraviolet light. The fetus/tissue was judged to be transgenic if a 500 bp fragment was visible.

To ensure the results Southern blots were performed with all tissue samples.

Results

In vitro Culture

Primordial germ cells could clearly be distinguished because of their morphology. There were large roundish cells with typical "blebbing" pseudopodial activity.

Figure 10:
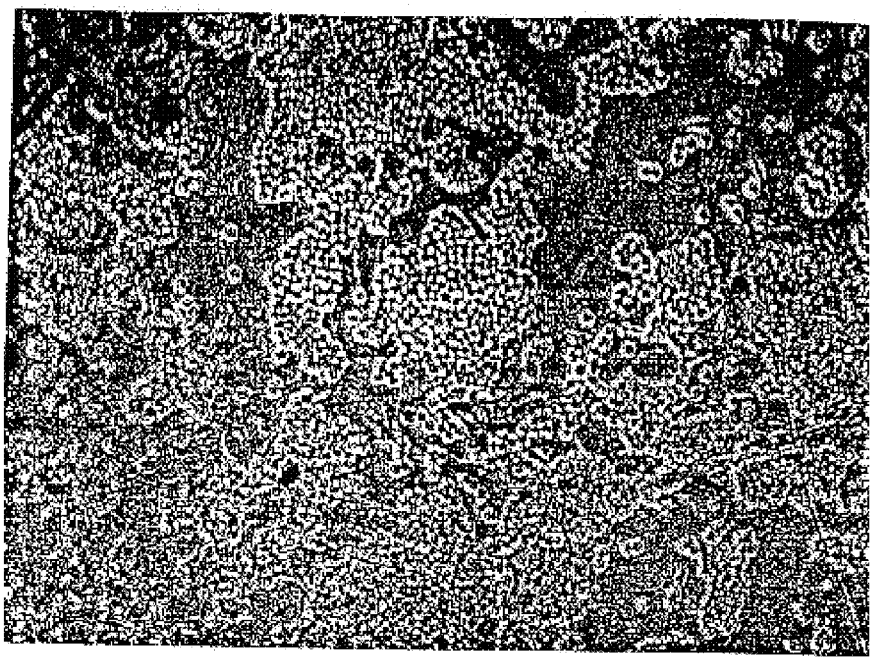
FIG. 10 shows the primary culture of PGCs in simple media to form single cells essentially as a monolayer.
Figure 11:
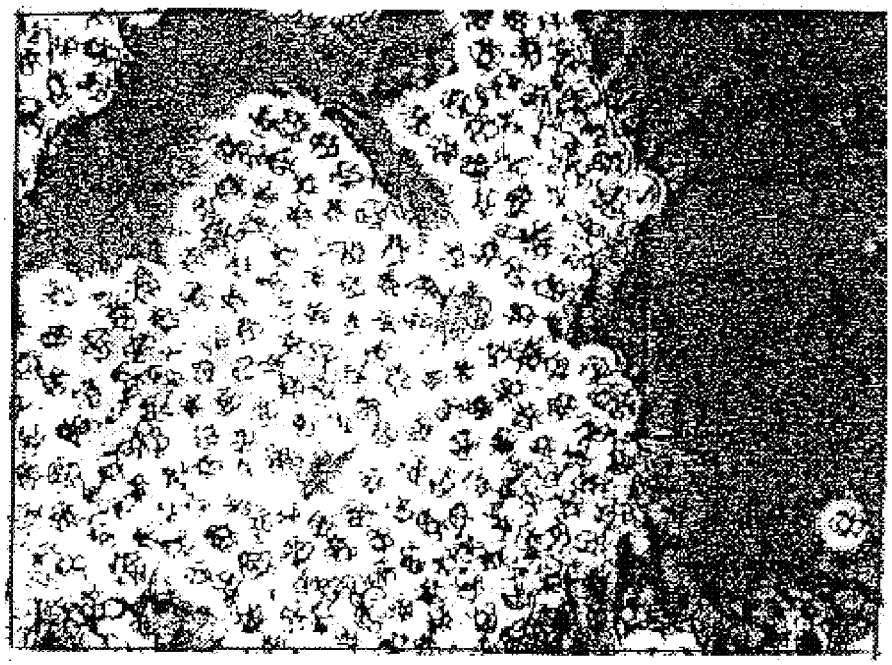
FIG. 11 shows a culture for the second passage of PGCs cultured in simple media to form single cells essentially as a monolayer.

When the culture conditions employed porcine PGCs seeded onto STO8 the culture showed proliferation about 7–8 days after isolation. In simple media the PGCs remained single cells, which formed nearly a monolayer. They very rarely formed colonies, in most of the cases there were aggregates of single cells up to passage 3–4 (FIGS. 10–11). The cells were passaged once per two weeks.

Figure 12:
FIG. 12 shows a culture for the third passage of PGCs cultured in simple media.
Figure 13:
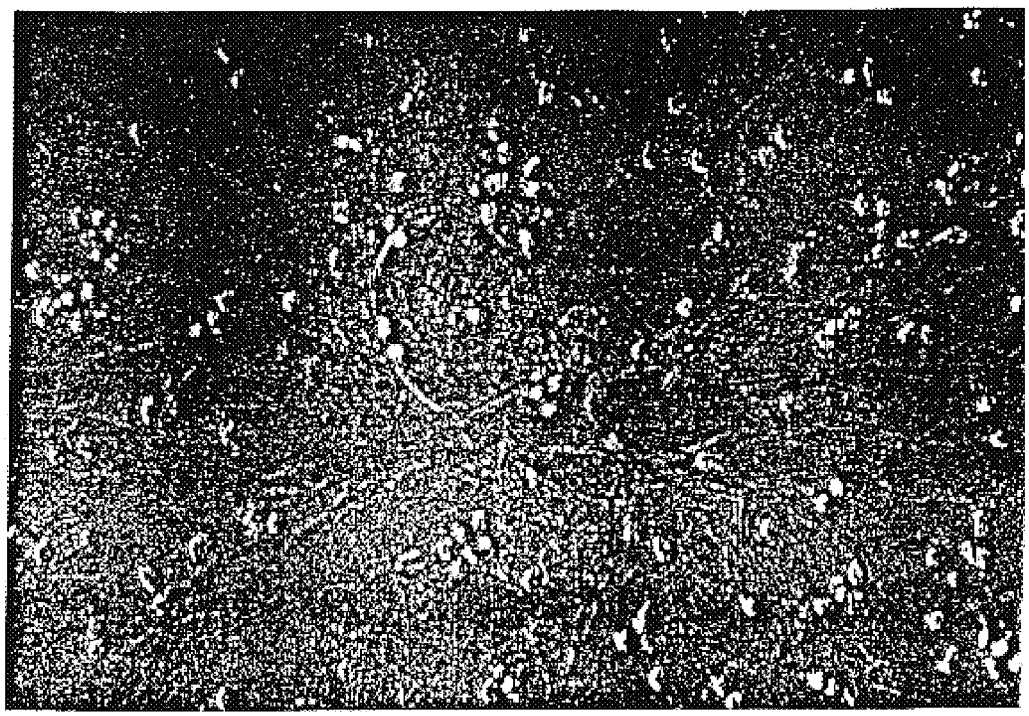
FIG. 13 shows a colony of porcine PGCs in primary culture which are seeded on STO8 feeder cells and cultivated in ES-cell media.
Figure 14:
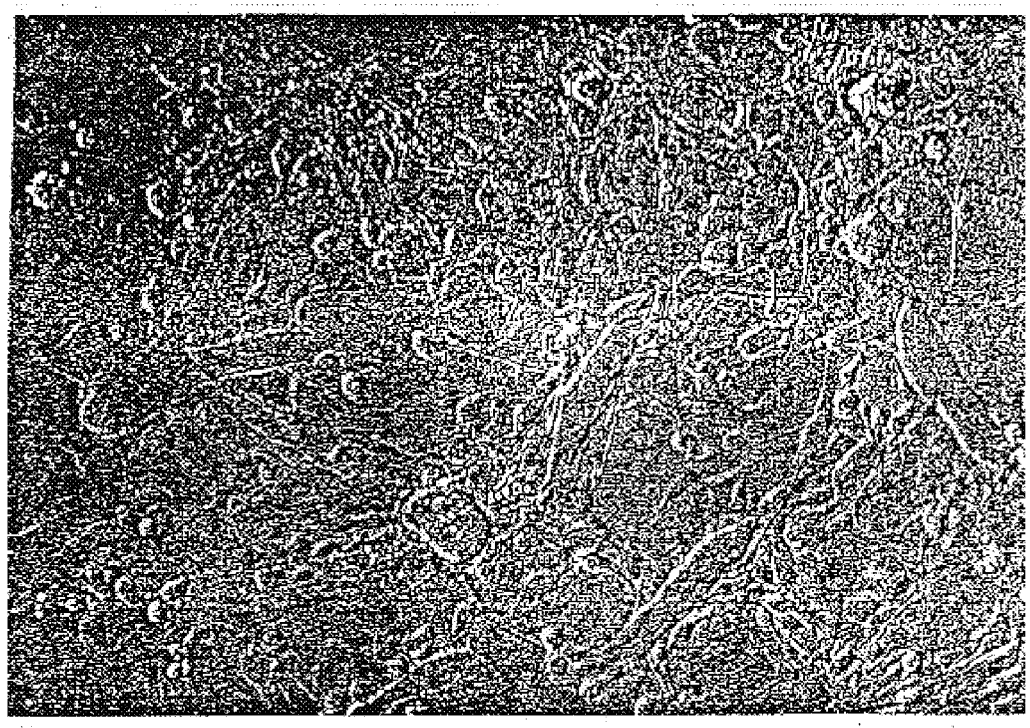
FIG. 14 shows PGC-derived colonies after the fifth passage which are cultivated in ES-cell media. The cells were passaged every two weeks.

In ES-cell medium according to Robertson (1987) 7–10 days after isolation the first densely packed colonies could be observed. Less single cells were detected and the PGCs were passaged once per week (FIGS. 12–14).

Porcine primordial germ cells/primordial germ cell-derived cells have been derived from 20 primary pools of genital ridges. Eight lines survived up to 13 passages and still are in culture. Various passages are cryopreserved.

Four PGC derived cells have been thawed. They survived cryopreservation and formed once again densely packed colonies in culture (FIGS. 15–16).

In long-term culture also differentiated cells could be detected. The primordial germ cells either differentiated into endodermal-like cells or fibroblast-like cells. If differentiation took place the remaining undifferentiated PGCs rapidly decreased in number and were overgrown by the other cells.

Staining

Figure 17:
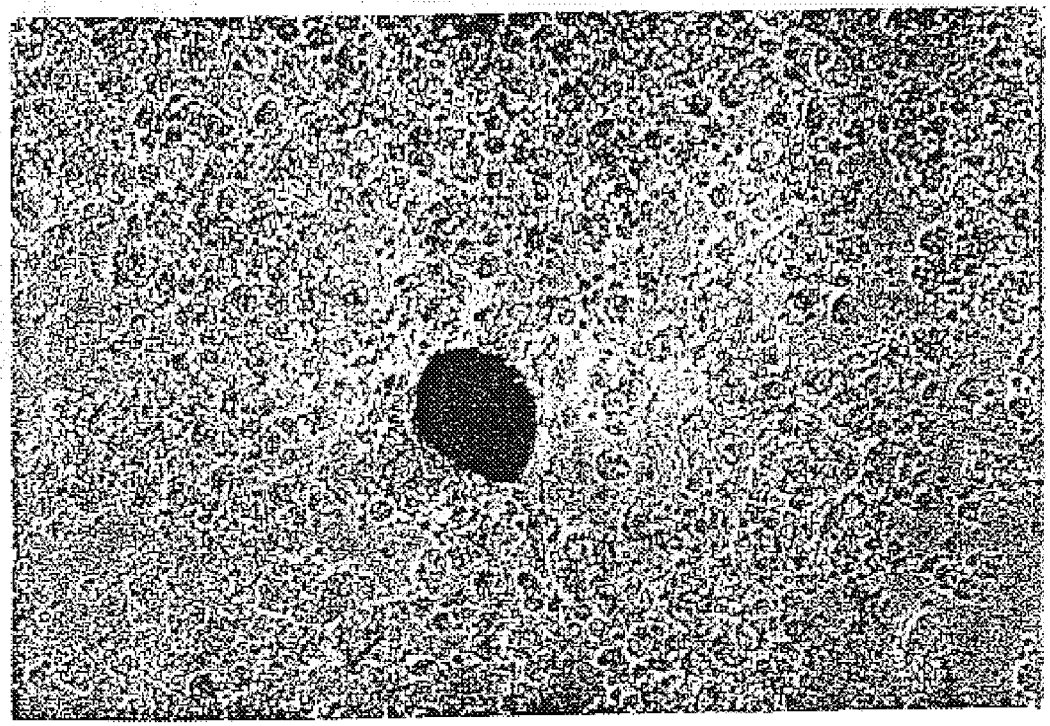
FIG. 17 shows AP staining of porcine PGCs after their third passage. The cells were passaged every two weeks.
Figure 18:
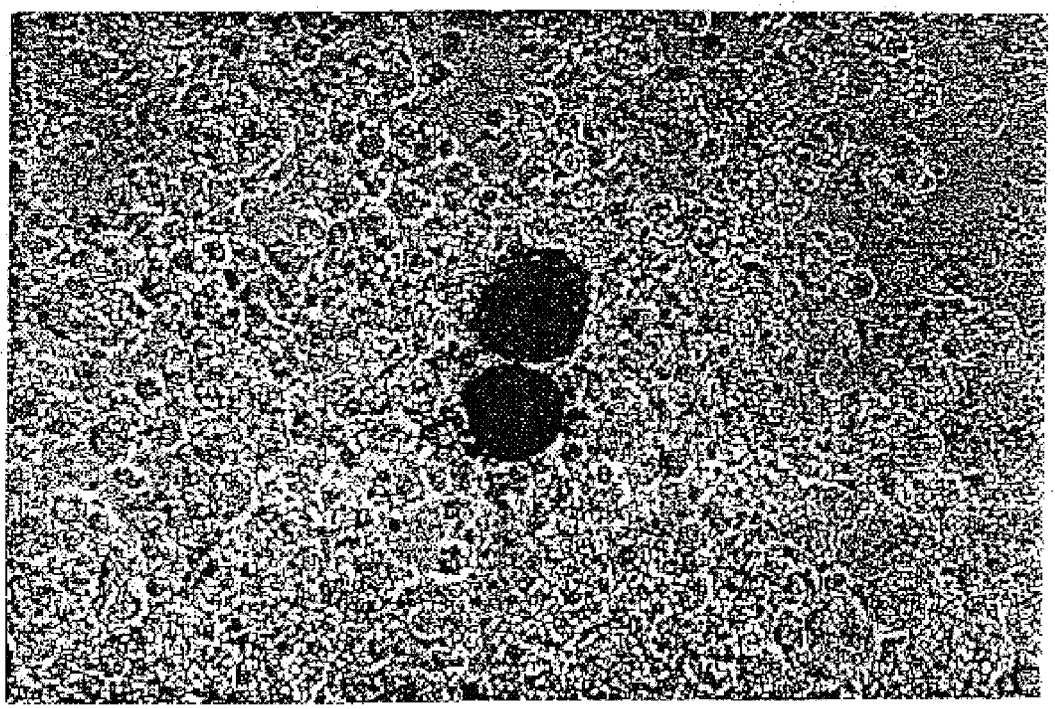
FIG. 18 shows AP staining of porcine PGCs after their fourth passage. The cells were passaged every two weeks.
Figure 19:
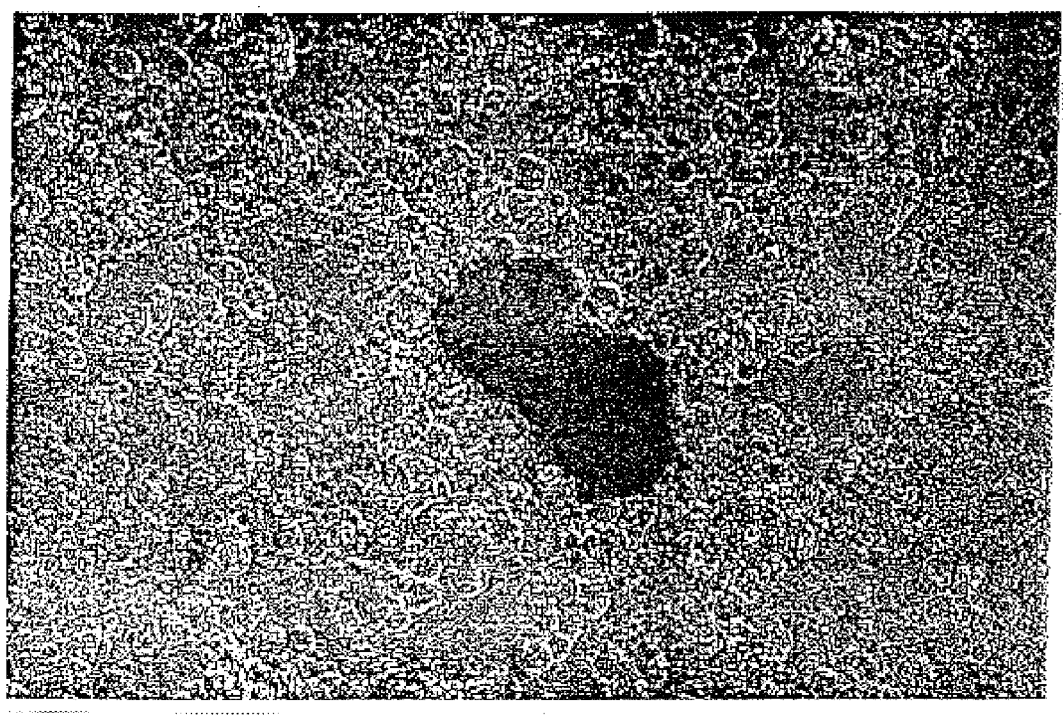
FIG. 19 shows AP staining of porcine PGCs after their fifth passage. The cells were passaged every two weeks.

AP positive cells were found in almost every sample we treated with the staining kit by Sigma. In primary culture AP positive single cells could be detected arranged near by small pieces of gonadal tissues which were still in the culture dishes. Different passages showed positive colonies (FIGS. 17–19).

Figure 20:
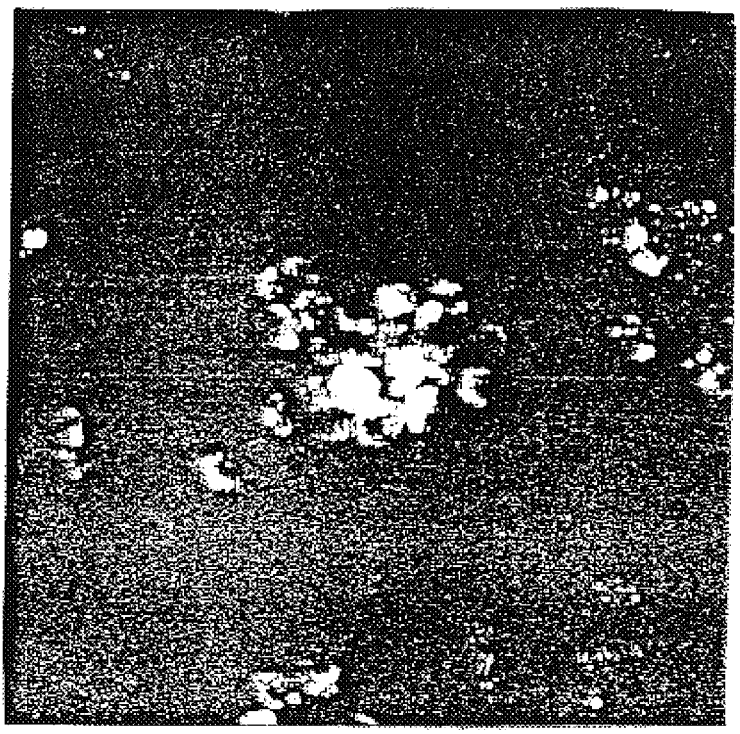
FIG. 20 shows porcine PGCs after four weeks of culturing which have been stained for SSEA-1 as analyzed by a Confocal Laser Scanning Microscope.
Figure 21:
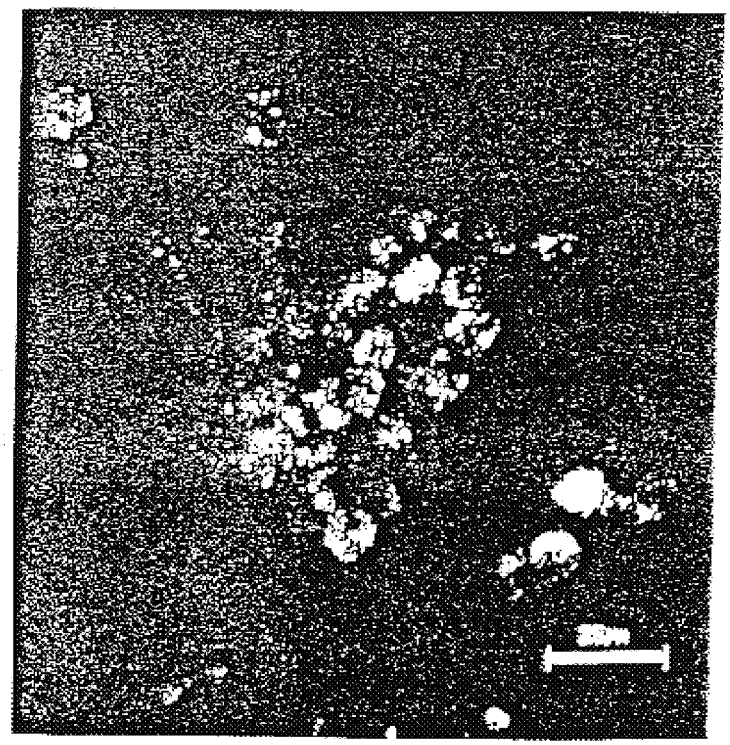
FIG. 21 shows porcine PGCs after four weeks of culturing which have been stained for SSEA-1 as analyzed by a Confocal Laser Scanning Microscope.
Figure 22:
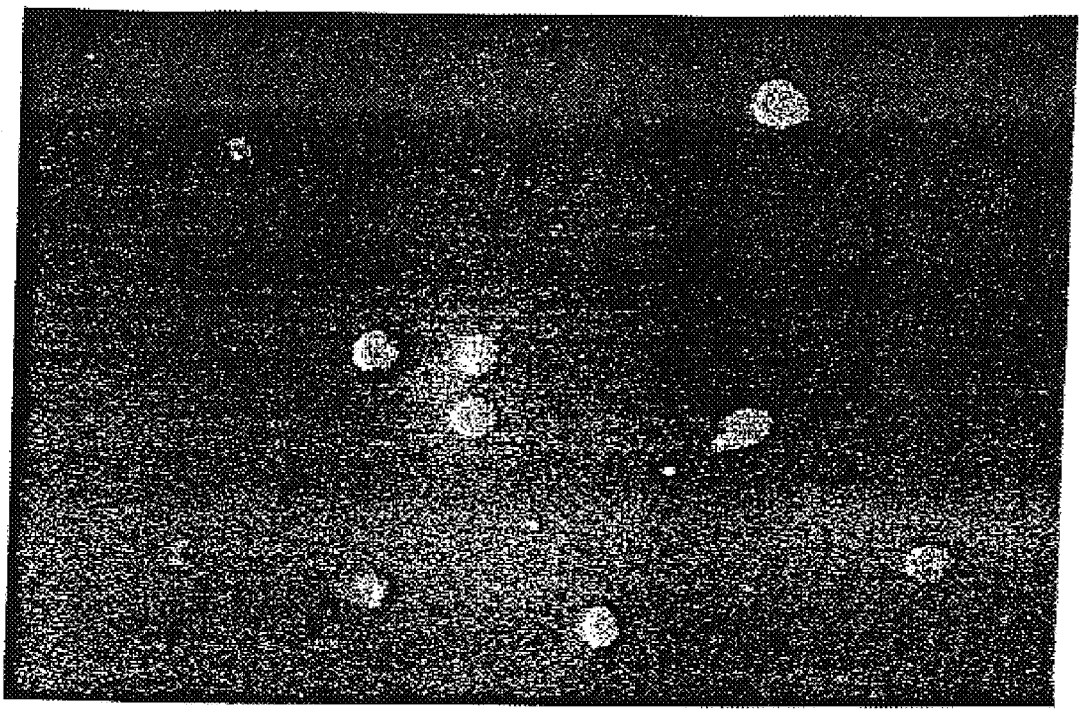
FIG. 22 shows SSEA-1 positive porcine PGCs after ten weeks in culture and the fifth passage. The cells were passaged every two weeks and the culture is stained for SSEA-1 and analyzed by a Confocal Laser Scanning Microscope.

Staining for SSEA-1 was Carried out at Different Stages
1. PGCs 4 weeks in culture on STO8 feeder, second passage (FIGS. 20–21)
2. PGCs 10 weeks in culture, fifth passage (FIG. 22)
3. Cryopreserved and thawed porcine PGCs third passage; cultivated until passage 5 and stained for SSEA-1 (FIG. 23).
4. PGCs cultured for 16 weeks on STO8, twelfth passage. (Data not shown.)
5. Cryopreserved and thawed cells which were cultivated up to passage twelfth. (Data not shown).

Pregnancy Rates After Transfer and Detection of Chimerism

More than 90% of the embryos survived microinjection and most of them re-expanded within two hours.

A total of 203 host blastcysts were injected with (a) freshly isolated PGCs, or (b) PGCs cultivated twenty hours or (c) PGCs cultivated for 4 days or (d) PGCs cryopreserved/thawed and cultivated for 4 weeks. Eleven transfers were performed in recipient gilts 24 hours asynchronous with the donors.

Six gilts became pregnant and five of them delivered 49 normal developed fetuses and showed 3 re-absorptions at slaughter. One transfer was carried out in a synchronous recipient, this gilt didn't become pregnant. All the 49 conceptuses resulting from injected embryos were analyzed.

Table 3 shows data of the Experiments (i) to (v) concerning the transfers and the number of normal developed fetuses.

TABLE 3

|  | Exp. (i) | Exp. (ii) | Exp. (iii) | Exp. (iv) | Exp. (v) |
| --- | --- | --- | --- | --- | --- |
| Age of PGC donor | Day 26 | Day 28 | Day 25 | Day 27 | Day 28 |
| Freshly isolated/ cultured/ thawed | Freshly isolated | 4 days IVC | 20 hours IVC | 20 hours IVC | thawed and 4 weeks IVC |
| Embryos transferred | 36 | 18 | 56 | 55 | 36 |
| No. of recipients | 2 | 1 | 3 | 3 | 2 |
| Pregnant recipients | 2 | 0 | 0 | 2 | 2 |
| Normal developed fetuses | 20 | 0 | 0 | 16 + 3 re-absorptions | 13 sec. |
| Detected chimeras | 12 | 0 | 0 | 11 | 9 |

Of the above 49 fetuses, 32 Exhibited chimerism in at least one of five tissues.

Tables 4–6 below show the data of PCR and Southern Blot for Experiments (i), (iv) and (v) above.

TABLE 4

Experiment (i)
(Chimerism Detected by PCR or by Blot = B or both)

| samples/ fetuses | skin | umbil | brain | heart | lungs | git | liver | kidney | gonad | placenta | spleen |
| --- | --- | --- | --- | --- | --- | --- | --- | --- | --- | --- | --- |
| DL-1 | — | — | — | B? | — | — | B? | — | — | — | B |
| DL-2 | — | — | — | — | — | — | — | B | — | — | B |
| DL-3 | — | — | — | — | — | B | — | B | — | — | — |
| DL-4 | — | — | — | B | — | — | — | B | — | — | — |
| DL-5 | B | — | — | — | B | B | — | — | — | — | — |
| DL-6 | B | — | — | — | — | — | — | — | — | — | — |
| DL-7 | — | — | — | — | — | — | — | — | — | — | — |
| DL-8 | — | — | — | — | — | — | — | — | — | — | — |
| D-1 | — | — | — | — | — | — | — | — | — | — | — |
| D-2 | — | — | B | — | — | — | — | — | — | — | — |
| D-3 | — | B | — | — | — | — | — | — | — | — | — |
| D-4 | — | — | — | — | — | — | — | — | — | — | — |
| D-5 | — | — | B | — | — | — | — | — | — | — | — |
| D-6 | B | — | — | — | — | — | — | — | — | — | — |
| D-7 | — | — | — | — | — | — | — | — | — | — | — |
| D-8 | — | — | — | — | — | — | — | — | — | — | — |
| D-9 | — | — | B | — | — | — | — | — | — | — | — |
| D-10 | — | — | — | — | — | — | — | — | — | — | — |
| D-11 | — | — | — | — | — | — | — | — | — | — | — |
| D-12 | B | — | — | — | — | — | — | B | — | — | — |

TABLE 5

Experiment (iv)
(Chimerism Detected by PCR or by Southern Blot = B)

| samples/fetuses | skin | umbil | brain | heart | lungs | git | liver | kidney | gonad | placenta | spleen | meso-neph. |
|---|---|---|---|---|---|---|---|---|---|---|---|---|
| DL-1 | — | — | — | B | B | — | — | — | — | — | — | — |
| DL-2 | — | — | — | — | — | — | — | — | — | — | — | — |
| DL-3 | B/PCR | B | — | — | B | B | — | — | — | B | — | — |
| DL-4 | — | B | — | — | — | — | — | — | — | B | — | — |
| DL-5 | — | B | — | B/PCR | B | B | — | — | — | — | — | — |
| DL-6 | — | — | — | B/PCR | — | — | — | — | — | B | — | — |
| DL-7 | B/PCR | — | — | B/PCR | — | — | — | — | — | — | — | — |
| DL-8 | — | — | — | B/PCR | — | B | — | — | — | — | — | — |
| DL-9 | B | — | B | — | — | — | — | — | — | — | — | — |
| DL-10 | — | — | — | — | — | — | — | — | — | — | — | — |
| DL-11 | — | — | — | — | — | — | — | — | — | — | — | — |
| D-1 | — | — | — | — | — | — | — | — | — | — | — | — |
| D-2 | — | — | — | — | — | — | — | — | — | — | — | — |
| D-3 | — | — | B | — | B | — | — | B/PCR | — | — | — | — |
| D-4 | — | — | — | — | — | — | — | — | — | — | — | — |
| D-5 | — | — | B | — | — | — | — | — | — | — | — | B |

TABLE 6

Experiment (v)
(Chimerism of Frozen/Thawed Cells by Southern Blot = B)

| samples/fetuses | skin | umbil | brain | heart | lungs | git | liver | kidney | gonad | placenta | spleen | meso-neph. |
|---|---|---|---|---|---|---|---|---|---|---|---|---|
| D-1 | — | — | — | — | — | — | — | — | — | — | — | — |
| D-2 | — | — | — | — | — | — | — | — | — | — | — | — |
| D-3 | B | — | — | — | — | — | — | — | — | — | — | — |
| D-4 | — | — | B | — | — | — | — | — | — | — | — | — |
| D-5 | — | — | — | — | — | — | — | — | — | — | — | — |
| D-6 | — | — | — | — | — | — | — | — | — | — | B | — |
| D-7 | — | — | — | — | — | — | — | — | B | — | — | — |
| D-8 | — | — | — | — | — | — | — | — | — | B | — | — |
| D-9 | — | — | — | — | — | — | — | — | — | — | B | — |
| D-10 | — | — | — | — | — | — | — | — | — | — | — | — |
| D-11 | — | — | B | — | — | — | — | — | — | — | — | — |
| D-12 | — | — | — | — | — | — | B | B | — | — | — | — |
| D-13 | — | — | B | — | — | — | — | — | B | — | — | — |

EXAMPLE 5
Blastocyst Injection with Porcine Totipotent Germ Cells

Porcine totipotent primordial cells from PGCs were injected into embryo blastocysts to demonstrate the ability of such cells to become germ cells in the fetus resulting from the injected embryo and cause such fetuses to have the ability to pass on the traits of the totipotent cells to their offspring.

Porcine totipotent cells are obtained from (1) Freshly isolated PGC suspensions (isolated as described in Example 2) which have the construct described in Example 4 or another detectable trait different from the blastocysts to be injected, (2) totipotent cells from long-term cultures as set forth in Examples 2 and 3 which have a detectable trait as described above, and (3) cryopreserved cells which have a detectable trait.

The totipotent cells thus obtained were seeded to either gelatin-coated dishes or to mitotically inactivated feeder layers of STO8 cells and cultured briefly in Dulbecco's modified Eagle's medium (DMEM), 10% heat inactivated fetal calf serum in an atmosphere of 5% $CO_2$ in air at 37° C. Five to ten cells phenotypically resembling PGCs (large round cells with typical "blebbing" pseudopodial activity) were injected into expanded blastocysts of the same sex as the cells of the totipotent cells at about 4 hours after preparation. Eighteen re-expanded embryos each were transferred to two recipients (24 hours asynchronous with the donors) into the tip of the uterine horns by endoscopy. The gilts were slaughtered after 5 weeks of pregnancy and 20 normal developed fetuses (8/12 per sow) were delivered.

Each fetus was dissected and eleven tissues were selected for DNA analysis by PCR to detect the WAP-hGH transgene (or other detectable trait) in skin/muscle, umbilical cord, brain, heart, lungs, gastrointestinal tract, liver, kidney, gonads, fetal placenta and spleen. The PCR data shows that the gonads of the embryos resulting from such injected blastocysts contain germ cells which correspond in genotype to the WAP-hGH transgene or other detectable trait.

Such data (not shown) demonstrates that initial PGCS, first passage cultured totipotent cells, long-term cultured totipotent cells and reconstituted cryopreserved totipotent cells all result in viable germ cells in the gonads of the injected embryos. Thus, the adult swine resulting from such embryos can be cross-mated or mated with wild-type adult to produce off-spring having the desired trait or transgene.

Such procedures will result in second generation offspring with the desired trait since the desired traits are generally present only in the germ cells or other tissues of the adult resulting from the injected embryo. The adult is usually phenotypically negative for the desired trait.

EXAMPLE 6
Injection of Enucleated Eggs with Porcine Totipotent Cells

Porcine totipotent cells from PGCs are injected into enucleated eggs (fertilized or unfertilized ovum from which the nucleus have been removed using standard methods well-known in the art) to demonstrate the ability of such cells to become total individuals homozygous for a desired trait. The fetuses and adults that result from such injected eggs have the desired trait phenotypically and genotypically as well the ability to pass on the trait of the totipotent cells to their offspring in a homozygous manner.

Porcine totipotent cells are obtained from (1) Freshly isolated PGC suspensions (isolated as described in Example 2) which have the construct described in Example 5 or another detectable trait different from the blastocysts to be injected, (2) totipotent cells from long-term cultures as set forth in Example 2 which have a detectable trait as described above, and (3) cryopreserved cells which have a detectable trait.

One or more of such porcine totipotent cells from such cultures is/are injected into the enucleated eggs using methods standard in the art and the embryos are then cultured until they are expanded embryos. Each of the resulting embryos is transferred to recipients who have been prepared for such embryo transfer using methods standard in the art by placing the embryos into the tip of the uterine horns by endoscopy. The gilts were slaughtered after 5 weeks of pregnancy and the normally developed fetuses are delivered. Each fetus is dissected and eleven tissues were selected for DNA analysis by PCR to detect the WAP-hGH transgene or other detectable trait: skin/muscle, umbilical cord, brain, heart, lungs, gastrointestinal tract, liver, kidney, gonads, fetal placenta and spleen. The PCR data shows that all of the tissues have the WAP-hGH transgene or other detectable trait. Thus, adults resulting from such embryos will have the desired trait of the totipotent cells as well as the ability to pass the trait on to offspring.

Such procedures result in a line of "identical twins" all having the desired trait of the totipotent cells which are the same sex as the totipotent cells.

Numerous modifications and variations of the present invention are possible in light of the above teachings and, therefore, within the scope of the appended claims, the invention may be practiced otherwise than as particularly described.

What is claimed is:

1. A composition comprising (i) porcine pluripotent cells and (ii) STO8 feeder cells which express a porcine stem cell factor.

2. The composition of claim 1 wherein said porcine stem cell factor is in membrane-bound form.

3. The composition of claim 1 wherein said porcine stem cell factor comprises an amino acid sequence selected from the group consisting of the amino acid sequence of SEQ ID NO: 5 and the amino acid sequence of SEQ ID NO: 9.

4. The composition of claim 3 wherein said porcine stem cell factor comprises an amino acid sequence having the sequence SEQ ID NO: 9.

5. The composition of claim 1 and further comprising at least one additional growth factor.

6. The composition of claim 5 wherein said at least one additional growth factor comprises LIF.

7. The composition of claim 5 wherein said at least one additional growth factor comprises bFGF.

8. The composition of claim 5 wherein said at least one additional growth factor comprises mouse stem cell factor.

9. A method of culturing a porcine pluripotent cell comprising culturing a porcine pluripotent cell in the presence of STO8 feeder cells which express a porcine stem cell factor.

10. The method of claim 9 wherein said porcine stem cell factor is in membrane-bound form.

11. The method of claim 9 wherein said porcine stem cell factor comprises an amino acid sequence selected from the group consisting of the amino acid sequence of SEQ ID NO: 5 and the amino acid sequence of SEQ ID NO: 9.

12. The method of claim 11 wherein said porcine stem cell factor comprises an amino acid sequence having the sequence SEQ ID NO: 9.

* * * * *

SEQUENCE LISTING

```
<160> NUMBER OF SEQ ID NOS:  11

<210> SEQ ID NO 1
<211> LENGTH: 952
<212> TYPE: DNA
<213> ORGANISM: Artificial
<220> FEATURE:
<221> NAME/KEY:
<222> LOCATION:
<223> OTHER INFORMATION: cDNA encoding porcine stem cell factor

<400> SEQUENCE: 1
gagctccaga acaggtaaac ggagttgcca caccgctgcc tgggctggat cacagcgctg      60
cctttccttt atg aag aag aca caa act tgg att atc act tgc att tat       108
            Met Lys Lys Thr Gln Thr Trp Ile Ile Thr Cys Ile Tyr
                -25                 -20                 -15 ctt caa ctg ctc cta ttt aat cct ctc gtc aga act caa ggg atc tgc      156
Leu Gln Leu Leu Leu Phe Asn Pro Leu Val Arg Thr Gln Gly Ile Cys
        -10                  -5                   1 agg aac cgt gtg act gat gat gtg aaa gac gtt aca aaa ttg gtg gca      204
Arg Asn Arg Val Thr Asp Asp Val Lys Asp Val Thr Lys Leu Val Ala
 5                   10                  15                  20 aat ctt cca aaa gac tat aag ata acc ctc aaa tat gtc ccc ggg atg      252
Asn Leu Pro Lys Asp Tyr Lys Ile Thr Leu Lys Tyr Val Pro Gly Met
                 25                  30                  35 gac gtt ttg cct agt cat tgt tgg ata agc gaa atg gtg gaa caa ctg      300
Asp Val Leu Pro Ser His Cys Trp Ile Ser Glu Met Val Glu Gln Leu
             40                  45                  50 tca gtc agc ttg act gat ctt ctg gac aag ttt tcc aat att tct gaa      348
Ser Val Ser Leu Thr Asp Leu Leu Asp Lys Phe Ser Asn Ile Ser Glu
         55                  60                  65 ggc ttg agt aat tat tct atc ata gac aaa ctt gtg aaa att gtt gat      396
Gly Leu Ser Asn Tyr Ser Ile Ile Asp Lys Leu Val Lys Ile Val Asp
     70                  75                  80 gac ctc gtg gaa tgc atg gaa gaa cac tca ttt gag aat gta aga aaa      444
Asp Leu Val Glu Cys Met Glu Glu His Ser Phe Glu Asn Val Arg Lys
 85                  90                  95                 100
```

```
tca tct aag agc cca gaa ccc agg ctg ttt act cct gaa aaa ttc ttt      492
Ser Ser Lys Ser Pro Glu Pro Arg Leu Phe Thr Pro Glu Lys Phe Phe
            105                 110                 115 ggg att ttt aat aga tcc atc gat gcc ttc aag gat ttg gag atg gtg      540
Gly Ile Phe Asn Arg Ser Ile Asp Ala Phe Lys Asp Leu Glu Met Val
        120                 125                 130 gca cct aaa act agt gaa tgt gtg att tct tca aca tta act cct gaa      588
Ala Pro Lys Thr Ser Glu Cys Val Ile Ser Ser Thr Leu Thr Pro Glu
            135                 140                 145 aaa gat tcc aga gtc agt gtc aca aaa cca ttt atg tta ccc cct gtt      636
Lys Asp Ser Arg Val Ser Val Thr Lys Pro Phe Met Leu Pro Pro Val
        150                 155                 160 gca gcc agc tcc ctt agg aat gac agc agt agc agt aat agg aaa gcc      684
Ala Ala Ser Ser Leu Arg Asn Asp Ser Ser Ser Ser Asn Arg Lys Ala
165                 170                 175                 180 tca gat tcg att gaa gac tcc agc ctc cag tgg gca gcg gta gca ttg      732
Ser Asp Ser Ile Glu Asp Ser Ser Leu Gln Trp Ala Ala Val Ala Leu
            185                 190                 195 cca gca ttc ttc tct ctt gtg att ggg ttt gct ttt gga gcc tta tac      780
Pro Ala Phe Phe Ser Leu Val Ile Gly Phe Ala Phe Gly Ala Leu Tyr
        200                 205                 210 tgg aag aag aaa caa cca aac ctt aca agg aca gtg gaa aat ata gag      828
Trp Lys Lys Lys Gln Pro Asn Leu Thr Arg Thr Val Glu Asn Ile Gln
            215                 220                 225 att aat gaa gag gat aat gag ata agt atg ttg caa gaa aaa gag aga      876
Ile Asn Glu Glu Asp Asn Glu Ile Ser Met Leu Gln Glu Lys Glu Arg
        230                 235                 240 gag ttt caa gaa gtg taa ttgtggcgtg tatcaacact gttgctttcg tacattgggt 934
Glu Phe Gln Glu Val
245 ggtaacagtt gatgtttg                                                  952

<210> SEQ ID NO 2
<211> LENGTH: 274
<212> TYPE: PRT
<213> ORGANISM: Artificial
<220> FEATURE:
<221> NAME/KEY:
<222> LOCATION:
<223> OTHER INFORMATION: Porcine stem cell factor

<400> SEQUENCE: 2

Met Lys Lys Thr Gln Thr Trp Ile Ile Thr Cys Ile Tyr Leu Gln
-25                 -20                 -15

Leu Leu Leu Phe Asn Pro Leu Val Arg Thr Gln Gly Ile Cys Arg
-10                 -5                   1                 5

Asn Arg Val Thr Asp Asp Val Lys Asp Val Thr Lys Leu Val Ala
                10                  15                  20

Asn Leu Pro Lys Asp Tyr Lys Ile Thr Leu Lys Tyr Val Pro Gly
                25                  30                  35

Met Asp Val Leu Pro Ser His Cys Trp Ile Ser Glu Met Val Glu
                40                  45                  50

Gln Leu Ser Val Ser Leu Thr Asp Leu Leu Asp Lys Phe Ser Asn
                55                  60                  65

Ile Ser Glu Gly Leu Ser Asn Tyr Ser Ile Ile Asp Lys Leu Val
                70                  75                  80

Lys Ile Val Asp Asp Leu Val Glu Cys Met Glu Glu His Ser Phe
                85                  90                  95
```

```
Glu Asn Val Arg Lys Ser Ser Lys Ser Pro Glu Pro Arg Leu Phe
                100                 105                 110

Thr Pro Glu Lys Phe Phe Gly Ile Phe Asn Arg Ser Ile Asp Ala
                115                 120                 125

Phe Lys Asp Leu Glu Met Val Ala Pro Lys Thr Ser Glu Cys Val
                130                 135                 140

Ile Ser Ser Thr Leu Thr Pro Glu Lys Asp Ser Arg Val Ser Val
                145                 150                 155

Thr Lys Pro Phe Met Leu Pro Pro Val Ala Ala Ser Ser Leu Arg
                160                 165                 170

Asn Asp Ser Ser Ser Asn Arg Lys Ala Ser Asp Ser Ile Glu
                175                 180                 185

Asp Ser Ser Leu Gln Trp Ala Ala Val Ala Leu Pro Ala Phe Phe
                190                 195                 200

Ser Leu Val Ile Gly Phe Ala Phe Gly Ala Leu Tyr Trp Lys Lys
                205                 210                 215

Lys Gln Pro Asn Leu Thr Arg Thr Val Glu Asn Ile Gln Ile Asn
                220                 225                 230

Glu Glu Asp Asn Glu Ile Ser Met Leu Gln Glu Lys Glu Arg Glu
                235                 240                 245

Phe Gln Glu Val
```

<210> SEQ ID NO 3
<211> LENGTH: 33
<212> TYPE: DNA
<213> ORGANISM: Artificial
<220> FEATURE:
<221> NAME/KEY:
<222> LOCATION:
<223> OTHER INFORMATION: PCR primer

<400> SEQUENCE: 3
ggtcaagctt cgctgccttt ccttatgaag aag                           33

<210> SEQ ID NO 4
<211> LENGTH: 33
<212> TYPE: DNA
<213> ORGANISM: Artificial
<220> FEATURE:
<221> NAME/KEY:
<222> LOCATION:
<223> OTHER INFORMATION: PCR primer

<400> SEQUENCE: 4
tccatctaga accacccaat gtacgaaagc aac                           33

<210> SEQ ID NO 5
<211> LENGTH: 633
<212> TYPE: DNA
<213> ORGANISM: Artificial
<220> FEATURE:
<221> NAME/KEY:
<222> LOCATION:
<223> OTHER INFORMATION: DNA encoding a soluble form of porcine stem
      cell factor

<400> SEQUENCE: 5

```
                                    gcgct gcctttcctt           15 atg aag aag aca caa act tgg att atc act tgc att tat ctt caa ctg   63
Met Lys Lys Thr Gln Thr Trp Ile Ile Thr Cys Ile Tyr Leu Gln Leu
-25                 -20                 -15                 -10
```

```
ctc cta ttt aat cct ctc gtc aga act caa ggg atc tgc agg aac cgt        111
Leu Leu Phe Asn Pro Leu Val Arg Thr Gln Gly Ile Cys Arg Asn Arg
            -5                   1               5 gtg act gat gat gtg aaa gac gtt aca aaa ttg gtg gca aat ctt cca        159
Val Thr Asp Asp Val Lys Asp Val Thr Lys Leu Val Ala Asn Leu Pro
        10                  15                  20 aaa gac tat aag ata acc ctc aaa tat gtc ccc ggg atg gac gtt ttg        207
Lys Asp Tyr Lys Ile Thr Leu Lys Tyr Val Pro Gly Met Asp Val Leu
    25                  30                  35 cct agt cat tgt tgg ata agc gaa atg gtg gaa caa ctg tca gtc agc        255
Pro Ser His Cys Trp Ile Ser Glu Met Val Glu Gln Leu Ser Val Ser
40                  45                  50                  55 ttg act gat ctt ctg gac aag ttt tcc aat att tct gaa ggc ttg agt        303
Leu Thr Asp Leu Leu Asp Lys Phe Ser Asn Ile Ser Glu Gly Leu Ser
                60                  65                  70 aat tat tct atc ata gac aaa ctt gtg aaa att gtt gat gac ctc gtg        351
Asn Tyr Ser Ile Ile Asp Lys Leu Val Lys Ile Val Asp Asp Leu Val
            75                  80                  85 gaa tgc atg gaa gaa cac tca ttt gag aat gta aga aaa tca tct aag        399
Glu Cys Met Glu Glu His Ser Phe Glu Asn Val Arg Lys Ser Ser Lys
        90                  95                 100 agc cca gaa ccc agg ctg ttt act cct gaa aaa ttc ttt ggg att ttt        447
Ser Pro Glu Pro Arg Leu Phe Thr Pro Glu Lys Phe Phe Gly Ile Phe
    105                 110                 115 aat aga tcc atc gat gcc ttc aag gat ttg gag atg gtg gca cct aaa        495
Asn Arg Ser Ile Asp Ala Phe Lys Asp Leu Glu Met Val Ala Pro Lys
120                 125                 130                 135 act agt gaa tgt gtg att tct tca aca tta act cct gaa aaa gat tcc        543
Thr Ser Glu Cys Val Ile Ser Ser Thr Leu Thr Pro Glu Lys Asp Ser
                140                 145                 150 aga gtc agt gtc aca aaa cca ttt atg tta ccc cct gtt gca gcc agc        591
Arg Val Ser Val Thr Lys Pro Phe Met Leu Pro Pro Val Ala Ala Ser
            155                 160                 165 tcc ctt agg aat gac agc agt agc agt aat agg aaa gcc taa                633
Ser Leu Arg Asn Asp Ser Ser Ser Ser Asn Arg Lys Ala
        170                 175                 180

<210> SEQ ID NO 6
<211> LENGTH: 68
<212> TYPE: DNA
<213> ORGANISM: Artificial
<220> FEATURE:
<221> NAME/KEY:
<222> LOCATION:
<223> OTHER INFORMATION: Oligonucleotide primer

<400> SEQUENCE: 6
atccatcgat gccttcaagg atttggagat ggtggcacct aaaactagtg aatgtgtgat    60
ttcttcaa                                                             68

<210> SEQ ID NO 7
<211> LENGTH: 65
<212> TYPE: DNA
<213> ORGANISM: Artificial
<220> FEATURE:
<221> NAME/KEY:
<222> LOCATION:
<223> OTHER INFORMATION: Oligonucleotide primer

<400> SEQUENCE: 7
tctgaggcct tcctattact ctactgctgt cattcccttt ttcaggagtt aatgttgaag    60
aaatc                                                                65
```

```
<210> SEQ ID NO 8
<211> LENGTH: 828
<212> TYPE: DNA
<213> ORGANISM: Artificial
<220> FEATURE:
<221> NAME/KEY:
<222> LOCATION:
<223> OTHER INFORMATION: DNA encoding active membrane-bound form of
      porcine stem cell factor

<400> SEQUENCE: 8
cgctgccttt cctt atg aag aag aca caa act tgg att atc act tgc att        50
             Met Lys Lys Thr Gln Thr Trp Ile Ile Thr Cys Ile
             -25             -20                 -15 tat ctt caa ctg ctc cta ttt aat cct ctc gtc aga act caa ggg atc        98
Tyr Leu Gln Leu Leu Leu Phe Asn Pro Leu Val Arg Thr Gln Gly Ile
            -10             -5                   1 tgc agg aac cgt gtg act gat gat gtg aaa gac gtt aca aaa ttg gtg       146
Cys Arg Asn Arg Val Thr Asp Asp Val Lys Asp Val Thr Lys Leu Val
  5              10                  15 gca aat ctt cca aaa gac tat aag ata acc ctc aaa tat gtc ccc ggg       194
Ala Asn Leu Pro Lys Asp Tyr Lys Ile Thr Leu Lys Tyr Val Pro Gly
 20              25                  30                      35 atg gac gtt ttg cct agt cat tgt tgg ata agc gaa atg gtg gaa caa       242
Met Asp Val Leu Pro Ser His Cys Trp Ile Ser Glu Met Val Glu Gln
                 40                  45                  50 ctg tca gtc agc ttg act gat ctt ctg gac aag ttt tcc aat att tct       290
Leu Ser Val Ser Leu Thr Asp Leu Leu Asp Lys Phe Ser Asn Ile Ser
                 55                  60                  65 gaa ggc ttg agt aat tat tct atc ata gac aaa ctt gtg aaa att gtt       338
Glu Gly Leu Ser Asn Tyr Ser Ile Ile Asp Lys Leu Val Lys Ile Val
             70                  75                  80 gat gac ctc gtg gaa tgc atg gaa gaa cac tca ttt gag aat gta aga       386
Asp Asp Leu Val Glu Cys Met Glu Glu His Ser Phe Glu Asn Val Arg
         85                  90                  95 aaa tca tct aag agc cca gaa ccc agg ctg ttt act cct gaa aaa ttc       434
Lys Ser Ser Lys Ser Pro Glu Pro Arg Leu Phe Thr Pro Glu Lys Phe
100             105                 110                 115 ttt ggg att ttt aat aga tcc atc gat gcc ttc aag gat ttg gag atg       482
Phe Gly Ile Phe Asn Arg Ser Ile Asp Ala Phe Lys Asp Leu Glu Met
                120                 125                 130 gtg gca cct aaa act agt gaa tgt gtg att tct tca aca tta act cct       530
Val Ala Pro Lys Thr Ser Glu Cys Val Ile Ser Ser Thr Leu Thr Pro
                135                 140                 145 gaa aaa ggg aat gac agc agt agc agt aat agg aaa gcc tca gat tcg       578
Glu Lys Gly Asn Asp Ser Ser Ser Ser Asn Arg Lys Ala Ser Asp Ser
            150                 155                 160 att gaa gac tcc agc ctc cag tgg gca gcg gta gca ttg cca gca ttc       626
Ile Glu Asp Ser Ser Leu Gln Trp Ala Ala Val Ala Leu Pro Ala Phe
            165                 170                 175 ttc tct ctt gtg att ggg ttt gct ttt gga gcc tta tac tgg aag aag       674
Phe Ser Leu Val Ile Gly Phe Ala Phe Gly Ala Leu Tyr Trp Lys Lys
180             185                 190                 195 aaa caa cca aac ctt aca agg aca gtg gaa aat ata gag att aat gaa       722
Lys Gln Pro Asn Leu Thr Arg Thr Val Glu Asn Ile Glu Ile Asn Glu
                200                 205                 210 gag gat aat gag ata agt atg ttg caa gaa aaa gag aga gag ttt caa       770
Glu Asp Asn Glu Ile Ser Met Leu Gln Glu Lys Glu Arg Glu Phe Gln
            215                 220                 225 gaa gtg taa ttgtggcgtg tatcaacact gttgctttcg tacattgggt ggttctaga    828
Glu Val
```

Glu Val

<210> SEQ ID NO 9
<211> LENGTH: 254
<212> TYPE: PRT
<213> ORGANISM: Artificial
<220> FEATURE:
<221> NAME/KEY:
<222> LOCATION:
<223> OTHER INFORMATION: Membrane-bound form of porcine stem cell factor

<400> SEQUENCE: 9

```
Met Lys Lys Thr Gln Thr Trp Ile Ile Thr Cys Ile Tyr Leu Gln
-25              -20              -15

Leu Leu Leu Phe Asn Pro Leu Val Arg Thr Gln Gly Ile Cys Arg
-10              -5                1                     5

Asn Arg Val Thr Asp Asp Val Lys Asp Val Thr Lys Leu Val Ala
                 10              15                      20

Asn Leu Pro Lys Asp Tyr Lys Ile Thr Leu Lys Tyr Val Pro Gly
                 25              30                      35

Met Asp Val Leu Pro Ser His Cys Trp Ile Ser Glu Met Val Glu
                 40              45                      50

Gln Leu Ser Val Ser Leu Thr Asp Leu Leu Asp Lys Phe Ser Asn
                 55              60                      65

Ile Ser Glu Gly Leu Ser Asn Tyr Ser Ile Ile Asp Lys Leu Val
                 70              75                      80

Lys Ile Val Asp Asp Leu Val Glu Cys Met Glu Glu His Ser Phe
                 85              90                      95

Glu Asn Val Arg Lys Ser Ser Lys Ser Pro Glu Pro Arg Leu Phe
                 100             105                     110

Thr Pro Glu Lys Phe Phe Gly Ile Phe Asn Arg Ser Ile Asp Ala
                 115             120                     125

Phe Lys Asp Leu Glu Met Val Ala Pro Lys Thr Ser Glu Cys Val
                 130             135                     140

Ile Ser Ser Thr Leu Thr Pro Glu Lys Gly Asn Asp Ser Ser Ser
                 145             150                     155

Ser Asn Arg Lys Ala Ser Asp Ser Ile Glu Asp Ser Ser Leu Gln
                 160             165                     170

Trp Ala Ala Val Ala Leu Pro Ala Phe Phe Ser Leu Val Ile Gly
                 175             180                     185

Phe Ala Phe Gly Ala Leu Tyr Trp Lys Lys Lys Gln Pro Asn Leu
                 190             195                     200

Thr Arg Thr Val Glu Asn Ile Gln Ile Asn Glu Glu Asp Asn Glu
                 205             210                     215

Ile Ser Met Leu Gln Glu Lys Glu Arg Glu Phe Gln Glu Val
                 220             225
```

<210> SEQ ID NO 10
<211> LENGTH: 29
<212> TYPE: DNA
<213> ORGANISM: Artificial
<220> FEATURE:
<221> NAME/KEY:
<222> LOCATION:
<223> OTHER INFORMATION: PCR primer

<400> SEQUENCE: 10
ccacccccaa agtcttcctc ctgtgggtc                                    29

-continued

```
<210> SEQ ID NO 11
<211> LENGTH: 20
<212> TYPE: DNA
<213> ORGANISM: Artificial
<220> FEATURE:
<221> NAME/KEY:
<222> LOCATION:
<223> OTHER INFORMATION: PCR primer

<400> SEQUENCE: 11
atgcgcaccc attccccaag                                              20
```